(12) United States Patent
Carter et al.

(10) Patent No.: US 7,848,801 B2
(45) Date of Patent: Dec. 7, 2010

(54) IONTOPHORETIC SYSTEMS, DEVICES, AND METHODS OF DELIVERY OF ACTIVE AGENTS TO BIOLOGICAL INTERFACE

(75) Inventors: Darrick Carter, Seattle, WA (US); Gregory A. Smith, Issaquah, WA (US)

(73) Assignee: TTI ellebeau, Inc., Tokyo (JP)

( * ) Notice: Subject to any disclaimer, the term of this patent is extended or adjusted under 35 U.S.C. 154(b) by 125 days.

(21) Appl. No.: 11/618,558

(22) Filed: Dec. 29, 2006

(65) Prior Publication Data
US 2008/0027369 A1 Jan. 31, 2008

Related U.S. Application Data

(60) Provisional application No. 60/755,391, filed on Dec. 30, 2005.

(51) Int. Cl.
*A61N 1/30* (2006.01)
(52) U.S. Cl. .............................................. 604/20
(58) Field of Classification Search ............ 604/20, 604/21
See application file for complete search history.

(56) References Cited

U.S. PATENT DOCUMENTS

| | | | | |
|---|---|---|---|---|
| 4,140,121 A | | 2/1979 | Kühl et al. ................ 128/260 |
| 4,374,168 A | | 2/1983 | Wojtowicz ................ 428/212 |
| 4,519,938 A | | 5/1985 | Papir ........................ 252/500 |
| 4,731,049 A | * | 3/1988 | Parsi ........................... 604/20 |
| 4,752,285 A | | 6/1988 | Petelenz et al. ............. 604/20 |
| 4,879,297 A | | 11/1989 | Mahjour et al. ........... 514/282 |
| 4,927,408 A | | 5/1990 | Haak et al. ................... 604/20 |
| 4,931,046 A | | 6/1990 | Newman ..................... 604/20 |
| 4,940,456 A | | 7/1990 | Sibalis et al. ................ 604/20 |
| 4,946,686 A | | 8/1990 | McClelland et al. ....... 424/473 |
| 5,057,072 A | | 10/1991 | Phipps ....................... 604/20 |
| 5,068,226 A | | 11/1991 | Weinshenker et al. ...... 514/58 |
| 5,073,539 A | * | 12/1991 | Mazzenga et al. ............ 514/2 |
| 5,080,646 A | | 1/1992 | Theeuwes et al. .......... 604/20 |
| 5,084,006 A | | 1/1992 | Lew et al. ................... 604/20 |
| 5,135,477 A | | 8/1992 | Untereker et al. .......... 604/20 |

(Continued)

FOREIGN PATENT DOCUMENTS

DE 101 36 403 2/2003

(Continued)

OTHER PUBLICATIONS

U.S. Appl. No. 11/616,666, filed Dec. 27, 2006, Smith.

(Continued)

*Primary Examiner*—Kevin C Sirmons
*Assistant Examiner*—Bradley J Osinski
(74) *Attorney, Agent, or Firm*—Hai Han; Seed IP Law Group PLLC

(57) ABSTRACT

A transdermal delivery device to passively deliver active agents to a biological interface includes an active agent reservoir comprising a first active agent of a first polarity; an outer active agent membrane taking the form of an ion-exchange membrane of a second polarity, an interfacial layer having a plurality of freely diffusible monovalent co-ions of the first polarity and having a first side adjacent to the outer active agent membrane and a second side configured to contact a biological interface.

9 Claims, 8 Drawing Sheets

U.S. PATENT DOCUMENTS

| | | |
|---|---|---|
| 5,147,296 A | 9/1992 | Theeuwes et al. .............. 604/20 |
| 5,158,537 A | 10/1992 | Haak et al. ..................... 604/20 |
| 5,162,043 A | 11/1992 | Lew et al. ...................... 604/20 |
| 5,169,383 A | 12/1992 | Gyory et al. ................... 604/20 |
| 5,203,768 A | 4/1993 | Haak et al. ..................... 604/20 |
| 5,224,927 A | 7/1993 | Tapper .......................... 604/20 |
| 5,240,995 A | 8/1993 | Gyory et al. ................... 525/57 |
| 5,290,585 A | 3/1994 | Elton ............................. 427/2 |
| 5,298,017 A | 3/1994 | Theeuwes et al. .............. 604/20 |
| 5,302,172 A | 4/1994 | Sage, Jr. et al. ................ 604/20 |
| 5,310,404 A | 5/1994 | Gyory et al. ................... 604/20 |
| 5,320,598 A | 6/1994 | Haak et al. ..................... 604/20 |
| 5,334,138 A | 8/1994 | Sage, Jr. et al. ................ 604/20 |
| 5,338,490 A | 8/1994 | Dietz et al. .................... 252/500 |
| 5,346,935 A | 9/1994 | Suzuki et al. .................. 524/18 |
| 5,362,420 A | 11/1994 | Itoh et al. ...................... 252/500 |
| 5,374,241 A | 12/1994 | Lloyd et al. .................... 604/20 |
| 5,380,272 A | 1/1995 | Gross ............................ 604/20 |
| 5,385,543 A | 1/1995 | Haak et al. ..................... 604/20 |
| 5,405,317 A | 4/1995 | Myers et al. ................... 604/20 |
| 5,415,866 A | 5/1995 | Zook ............................ 424/448 |
| 5,423,737 A | 6/1995 | Cartmell et al. ................ 602/57 |
| 5,423,739 A | 6/1995 | Phipps et al. ................... 604/20 |
| 5,489,624 A | 2/1996 | Kantner et al. ................. 524/376 |
| 5,525,356 A | 6/1996 | Jevne et al. .................... 424/484 |
| 5,536,768 A | 7/1996 | Kantner et al. ................. 524/376 |
| 5,540,654 A | 7/1996 | Riviere et al. .................. 604/20 |
| 5,558,633 A | 9/1996 | Phipps et al. ................... 604/20 |
| 5,573,503 A | 11/1996 | Untereker et al. .............. 604/20 |
| 5,573,668 A | 11/1996 | Grosh et al. ................... 210/490 |
| 5,582,587 A | 12/1996 | Gyory et al. ................... 604/20 |
| 5,637,084 A | 6/1997 | Kontturi et al. ................ 604/20 |
| 5,647,844 A * | 7/1997 | Haak et al. ..................... 604/20 |
| 5,660,178 A | 8/1997 | Kantner et al. ................. 128/640 |
| 5,668,170 A | 9/1997 | Gyory .......................... 514/449 |
| 5,711,761 A | 1/1998 | Untereker et al. .............. 604/20 |
| 5,718,913 A | 2/1998 | Dhuique-Mayer et al. .. 424/449 |
| 5,730,716 A | 3/1998 | Beck et al. ..................... 604/20 |
| 5,738,647 A | 4/1998 | Bernhard et al. ............... 604/20 |
| 5,770,627 A | 6/1998 | Inoue et al. .................... 514/772.1 |
| 5,788,666 A | 8/1998 | Atanasoska .................... 604/20 |
| 5,795,321 A | 8/1998 | McArthur et al. .............. 604/20 |
| 5,800,685 A | 9/1998 | Perrault ........................ 204/291 |
| 5,804,318 A | 9/1998 | Pinchuk et al. ................ 428/421 |
| 5,837,281 A | 11/1998 | Iga et al. ....................... 424/449 |
| 5,840,056 A * | 11/1998 | Atanasoska .................... 604/20 |
| 5,882,676 A | 3/1999 | Lee et al. ....................... 424/449 |
| 5,882,677 A | 3/1999 | Kupperblatt ................... 424/449 |
| 5,891,581 A | 4/1999 | Simpson et al. ................ 428/458 |
| 5,894,021 A | 4/1999 | Okabe et al. ................... 424/449 |
| 5,909,905 A | 6/1999 | Simpson et al. ............... 29/25.35 |
| 5,910,306 A | 6/1999 | Alving et al. .................. 424/184.1 |
| 5,911,223 A | 6/1999 | Weaver et al. ................. 128/898 |
| 5,928,185 A | 7/1999 | Muller et al. ................... 604/20 |
| 5,941,843 A | 8/1999 | Atanasoska .................... 604/20 |
| 5,942,245 A | 8/1999 | Katinger et al. ................ 424/450 |
| 5,976,101 A | 11/1999 | Sibalis .......................... 604/20 |
| 5,980,898 A | 11/1999 | Glenn et al. ................... 424/184.1 |
| 5,990,179 A | 11/1999 | Gyory et al. ................... 514/970 |
| 5,991,655 A | 11/1999 | Gross et al. ................... 604/20 |
| 5,993,435 A | 11/1999 | Haak et al. ..................... 604/501 |
| 5,995,869 A | 11/1999 | Cormier et al. ................ 604/20 |
| 6,006,130 A * | 12/1999 | Higo et al. ..................... 604/20 |
| 6,032,073 A | 2/2000 | Effenhauser .................. 604/20 |
| 6,039,977 A | 3/2000 | Venkatraman et al. ....... 424/486 |
| 6,048,545 A | 4/2000 | Keller et al. ................... 424/450 |
| 6,064,908 A | 5/2000 | Muller et al. ................... 604/20 |
| 6,110,488 A | 8/2000 | Hoffmann .................... 424/449 |
| 6,119,036 A | 9/2000 | Allen, Jr. ...................... 604/20 |
| 6,165,500 A | 12/2000 | Ceve ........................... 424/450 |
| 6,169,920 B1 | 1/2001 | Haak et al. ..................... 604/20 |
| 6,197,324 B1 | 3/2001 | Crittenden .................... 424/423 |
| 6,223,075 B1 | 4/2001 | Beck et al. ..................... 604/20 |
| 6,256,533 B1 | 7/2001 | Yuzhakov et al. .............. 604/21 |
| 6,258,276 B1 | 7/2001 | Mika et al. .................... 210/638 |
| 6,275,728 B1 | 8/2001 | Venkatraman et al. ........ 604/20 |
| 6,289,241 B1 | 9/2001 | Phipps .......................... 604/20 |
| 6,306,404 B1 | 10/2001 | LaPosta et al. ............. 424/278.1 |
| 6,312,612 B1 | 11/2001 | Sherman et al. ................. 216/2 |
| 6,317,630 B1 | 11/2001 | Gross et al. ................... 604/20 |
| 6,319,901 B1 | 11/2001 | Bernard et al. ................ 514/16 |
| 6,329,488 B1 | 12/2001 | Terry et al. ................... 528/28 |
| 6,330,471 B1 | 12/2001 | Higo et al. ..................... 604/20 |
| 6,334,856 B1 | 1/2002 | Allen et al. .................... 604/191 |
| 6,348,558 B1 | 2/2002 | Harris et al. ................... 528/196 |
| 6,350,259 B1 | 2/2002 | Sage, Jr. et al. ............... 604/501 |
| 6,375,945 B1 | 4/2002 | Boon et al. .................... 424/85.2 |
| 6,375,963 B1 | 4/2002 | Repka et al. ................... 424/402 |
| 6,377,847 B1 | 4/2002 | Keusch et al. ................. 604/20 |
| 6,379,324 B1 | 4/2002 | Gartstein et al. ............... 604/22 |
| 6,433,013 B1 | 8/2002 | Verschoor et al. ............ 514/557 |
| 6,451,240 B1 | 9/2002 | Sherman et al. .............. 264/504 |
| 6,471,903 B2 | 10/2002 | Sherman et al. ........... 264/328.1 |
| 6,477,410 B1 | 11/2002 | Henley et al. .................. 604/20 |
| 6,491,919 B2 | 12/2002 | Crane ......................... 424/184.1 |
| 6,496,727 B1 | 12/2002 | Bernhard et al. ............... 604/20 |
| 6,497,887 B1 | 12/2002 | Zecchino et al. .............. 424/401 |
| 6,503,231 B1 | 1/2003 | Prausnitz et al. ............. 604/272 |
| 6,511,463 B1 | 1/2003 | Wood et al. ................... 604/272 |
| 6,532,386 B2 * | 3/2003 | Sun et al. ....................... 604/20 |
| 6,533,949 B1 | 3/2003 | Yeshurun et al. ............. 216/11 |
| 6,565,532 B1 | 5/2003 | Yuzhakov et al. ............ 604/142 |
| 6,576,261 B1 | 6/2003 | Pitha .......................... 424/484 |
| 6,576,712 B2 | 6/2003 | Feldstein et al. ......... 525/326.9 |
| 6,596,401 B1 | 7/2003 | Terry et al. ................... 428/447 |
| 6,603,987 B2 | 8/2003 | Whitson ...................... 600/345 |
| 6,611,707 B1 | 8/2003 | Prausnitz et al. .............. 604/21 |
| 6,629,968 B1 | 10/2003 | Jain et al. ..................... 604/501 |
| 6,630,161 B1 | 10/2003 | Leesman ..................... 424/455 |
| 6,635,045 B2 | 10/2003 | Keusch et al. ................ 604/501 |
| 6,635,261 B2 | 10/2003 | LaPosta et al. ............. 424/278.1 |
| 6,645,495 B1 | 11/2003 | Kensil et al. ................. 424/184.1 |
| 6,649,170 B1 | 11/2003 | Lindblad et al. ........... 424/248.1 |
| 6,654,635 B1 | 11/2003 | Koga et al. ................... 604/20 |
| 6,663,820 B2 | 12/2003 | Arias et al. ................... 264/496 |
| 6,678,554 B1 | 1/2004 | Sun et al. ....................... 604/20 |
| 6,692,456 B1 | 2/2004 | Eppstein et al. .............. 604/22 |
| 6,735,470 B2 | 5/2004 | Henley et al. .................. 604/20 |
| 6,743,432 B1 * | 6/2004 | Yanai et al. ................... 424/400 |
| 6,767,341 B2 | 7/2004 | Cho ............................ 604/272 |
| 6,775,569 B2 | 8/2004 | Mori et al. .................... 604/20 |
| 6,775,570 B2 | 8/2004 | Joshi ........................... 604/20 |
| 6,790,372 B2 | 9/2004 | Roy et al. ..................... 216/10 |
| 6,797,276 B1 | 9/2004 | Glenn et al. ................ 424/278.1 |
| 6,803,420 B2 | 10/2004 | Cleary et al. ................. 525/205 |
| 6,815,360 B1 | 11/2004 | Canham et al. .............. 438/706 |
| 6,861,410 B1 | 3/2005 | Ott et al. ...................... 514/26 |
| 6,862,473 B2 | 3/2005 | Keusch et al. ................. 604/20 |
| 6,881,203 B2 | 4/2005 | Delmore et al. ............. 604/272 |
| 6,908,453 B2 | 6/2005 | Fleming et al. .............. 604/173 |
| 6,908,681 B2 | 6/2005 | Terry et al. ................... 428/447 |
| 6,918,901 B1 | 7/2005 | Theeuwes et al. ............ 604/500 |
| 6,939,311 B2 | 9/2005 | Geiger ........................ 600/573 |
| 6,975,902 B2 | 12/2005 | Phipps et al. ................. 604/20 |
| 7,018,370 B2 | 3/2006 | Southam et al. ............. 604/501 |
| 7,033,598 B2 | 4/2006 | Lerner ......................... 424/400 |
| 7,037,499 B1 | 5/2006 | Glenn et al. ................. 424/184.1 |
| 7,047,069 B2 | 5/2006 | Joshi ........................... 604/20 |
| 7,054,682 B2 | 5/2006 | Young et al. .................. 604/20 |
| 7,063,859 B1 | 6/2006 | Kanios et al. ................ 424/448 |
| 7,147,862 B1 | 12/2006 | Prieels et al. .............. 424/208.1 |
| 7,392,080 B2 | 6/2008 | Eppstein et al. .............. 604/20 |
| 2002/0028766 A1 * | 3/2002 | Papadimitriou ................ 514/2 |
| 2002/0035346 A1 | 3/2002 | Reynolds et al. .............. 604/20 |

| | | | |
|---|---|---|---|
| 2002/0048596 A1 | 4/2002 | Cevc | 424/450 |
| 2002/0058903 A1 | 5/2002 | Murdock | 604/20 |
| 2002/0123678 A1 | 9/2002 | Lerner et al. | 600/378 |
| 2003/0018295 A1 | 1/2003 | Henley et al. | 604/20 |
| 2003/0068361 A1 | 4/2003 | Margalit | 424/450 |
| 2003/0077324 A1 | 4/2003 | Mulve | 424/468 |
| 2003/0107149 A1 | 6/2003 | Yang et al. | 264/134 |
| 2003/0135150 A1 | 7/2003 | Kuribayashi et al. | 604/20 |
| 2003/0166773 A1 | 9/2003 | Chen et al. | 525/70 |
| 2003/0168404 A1 | 9/2003 | Mika et al. | 210/639 |
| 2003/0191426 A1 | 10/2003 | Lerner et al. | 604/20 |
| 2004/0034336 A1 | 2/2004 | Scott et al. | 604/890.1 |
| 2004/0044304 A1 | 3/2004 | Hill et al. | 604/20 |
| 2004/0071765 A1 | 4/2004 | Adachi et al. | 424/449 |
| 2004/0082901 A1 | 4/2004 | Phipps et al. | 604/20 |
| 2004/0087671 A1 | 5/2004 | Tamada et al. | 516/99 |
| 2004/0089533 A1 * | 5/2004 | Hoagland et al. | 204/192.11 |
| 2004/0105834 A1 | 6/2004 | Singh et al. | 424/70.13 |
| 2004/0127986 A1 | 7/2004 | Chen et al. | 623/11.11 |
| 2004/0137004 A1 | 7/2004 | Glenn et al. | 424/184.1 |
| 2004/0143210 A1 | 7/2004 | Shevlin | 604/20 |
| 2004/0166147 A1 | 8/2004 | Lundy et al. | 424/449 |
| 2004/0176737 A1 | 9/2004 | Henley et al. | 604/20 |
| 2004/0203149 A1 | 10/2004 | Childs et al. | 435/404 |
| 2004/0225253 A1 | 11/2004 | Shevlin | 604/20 |
| 2004/0247655 A1 | 12/2004 | Asmus et al. | 424/449 |
| 2004/0267169 A1 | 12/2004 | Sun et al. | 601/15 |
| 2004/0267232 A1 | 12/2004 | Sun et al. | 604/500 |
| 2004/0267236 A1 | 12/2004 | Sun et al. | 604/501 |
| 2005/0011826 A1 | 1/2005 | Childs et al. | 210/490 |
| 2005/0055014 A1 | 3/2005 | Coppeta et al. | 604/890.1 |
| 2005/0070840 A1 | 3/2005 | Matsumura et al. | 604/20 |
| 2005/0080012 A1 | 4/2005 | Mickle et al. | 514/12 |
| 2005/0123565 A1 | 6/2005 | Subramony et al. | 424/234.1 |
| 2005/0136638 A1 | 6/2005 | Voss-Kehl et al. | 438/610 |
| 2005/0143686 A1 | 6/2005 | Shevlin | 604/20 |
| 2005/0169976 A1 | 8/2005 | Mori et al. | 424/449 |
| 2005/0196343 A1 | 9/2005 | Reddy et al. | 424/9.322 |
| 2005/0197618 A1 | 9/2005 | Plummer et al. | 604/20 |
| 2005/0267440 A1 | 12/2005 | Herman et al. | 604/501 |
| 2005/0271725 A1 | 12/2005 | Kuribayashi et al. | 424/486 |
| 2005/0288621 A1 | 12/2005 | Phipps et al. | 604/20 |
| 2006/0002959 A1 | 1/2006 | Glenn et al. | 424/209.1 |
| 2006/0009730 A2 | 1/2006 | Shevlin | 604/20 |
| 2006/0024358 A1 | 2/2006 | Santini, Jr. et al. | 424/448 |
| 2006/0024359 A1 | 2/2006 | Walker et al. | 424/450 |
| 2006/0052739 A1 | 3/2006 | Henley et al. | 604/20 |
| 2006/0089590 A1 | 4/2006 | Higuchi et al. | 604/20 |
| 2006/0089591 A1 | 4/2006 | Nagashima et al. | 604/20 |
| 2006/0135906 A1 | 6/2006 | Matsumura et al. | 604/20 |
| 2006/0161097 A1 | 7/2006 | Domb | 604/20 |
| 2006/0171917 A1 | 8/2006 | Campbell et al. | 424/85.1 |
| 2006/0235351 A1 | 10/2006 | Matsumura et al. | 604/20 |
| 2006/0241548 A1 | 10/2006 | Fukuta et al. | 604/20 |
| 2006/0269593 A1 | 11/2006 | Glenn et al. | 424/450 |
| 2007/0048362 A1 | 3/2007 | Nakayama et al. | 424/449 |
| 2007/0060862 A1 | 3/2007 | Sun et al. | 604/20 |
| 2007/0078374 A1 | 4/2007 | Smith | 604/20 |
| 2007/0078375 A1 | 4/2007 | Smith | 604/20 |
| 2007/0083147 A1 | 4/2007 | Smith | 604/20 |
| 2007/0083185 A1 | 4/2007 | Carter | 604/501 |
| 2007/0083186 A1 | 4/2007 | Carter et al. | 604/501 |
| 2007/0088243 A1 | 4/2007 | Carter | 604/20 |
| 2007/0088332 A1 | 4/2007 | Akiyama et al. | 604/890.1 |
| 2007/0093787 A1 | 4/2007 | Smith | 604/890.1 |
| 2007/0100274 A1 | 5/2007 | Young et al. | 604/20 |
| 2007/0110810 A1 | 5/2007 | Smith | 424/486 |
| 2007/0135754 A1 | 6/2007 | Akiyama et al. | 604/20 |
| 2007/0225632 A1 | 9/2007 | Rauser et al. | 604/20 |
| 2008/0004564 A1 | 1/2008 | Smith | 604/20 |
| 2008/0033338 A1 | 2/2008 | Smith | 604/20 |
| 2008/0058701 A1 | 3/2008 | Smith | 604/20 |
| 2008/0175895 A1 | 7/2008 | Kogure et al. | 424/450 |
| 2008/0193514 A1 | 8/2008 | Kogure et al. | 424/450 |

FOREIGN PATENT DOCUMENTS

| | | |
|---|---|---|
| EP | 0 388 306 A2 | 9/1990 |
| EP | 0 537 998 A1 | 4/1993 |
| EP | 0 750 849 A1 | 1/1997 |
| EP | 0 813 879 A2 | 12/1997 |
| EP | 0 824 003 | 2/1998 |
| EP | 0 904 779 A2 | 3/1999 |
| EP | 0 974 364 A1 | 1/2000 |
| EP | 1 440 707 A1 | 7/2004 |
| EP | 1 547 579 A1 | 6/2005 |
| EP | 1 566 197 A1 | 8/2005 |
| FR | 2 787 729 A1 | 6/2000 |
| GB | 2 141 025 A | 12/1984 |
| GB | 2 265 088 A | 9/1993 |
| JP | 63-035266 | 2/1988 |
| JP | 2-91017 | 3/1990 |
| JP | 02-206474 | 8/1990 |
| JP | 7-503978 | 4/1995 |
| JP | 08-052224 | 2/1996 |
| JP | 08-503875 | 4/1996 |
| JP | 08-164212 | 6/1996 |
| JP | 08-317996 | 12/1996 |
| JP | 9-248344 | 9/1997 |
| JP | 09-255561 | 9/1997 |
| JP | 10-148942 | 6/1998 |
| JP | 11-076428 | 3/1999 |
| JP | 11-503043 | 3/1999 |
| JP | 11-503956 | 4/1999 |
| JP | 11-273452 | 10/1999 |
| JP | 3-40517 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2001-055332 | 2/2001 |
| JP | 2001-070459 | 3/2001 |
| JP | 2002-541934 | 12/2002 |
| JP | 2003-501379 | 1/2003 |
| JP | 2004-518707 | 6/2004 |
| JP | 2004-188188 | 7/2004 |
| JP | 2004-188390 | 7/2004 |
| JP | 2004-231575 | 8/2004 |
| JP | 2004-292438 | 10/2004 |
| JP | 2004-317317 | 10/2004 |
| JP | 2004-357313 | 12/2004 |
| JP | 2005-220222 | 8/2005 |
| JP | 2006-149891 | 6/2006 |
| JP | 2006-212194 | 8/2006 |
| JP | 2006-238839 | 9/2006 |
| JP | 2006-241110 | 9/2006 |
| JP | 2006-262943 | 10/2006 |
| KR | 2004-0016035 | 2/2004 |
| KR | 2004-0111227 | 12/2004 |
| KR | 2005-0018200 | 2/2005 |
| WO | WO 91/15250 | 10/1991 |
| WO | WO 92/03122 | 3/1992 |
| WO | WO 92/07618 | 5/1992 |
| WO | WO 97/48444 A1 | 12/1997 |
| WO | WO 98/17250 | 4/1998 |
| WO | WO 98/17377 | 4/1998 |
| WO | WO 99/00113 | 1/1999 |
| WO | WO 99/16434 | 4/1999 |
| WO | WO 00/47274 A1 | 8/2000 |
| WO | WO 00/74772 | 12/2000 |
| WO | WO 03/008078 | 1/2003 |
| WO | WO 03/034900 A2 | 5/2003 |

| WO | WO 03/037425 | 5/2003 |
| --- | --- | --- |
| WO | WO 2004/017941 | 3/2004 |
| WO | WO 2004/073843 | 9/2004 |
| WO | WO 2007/026672 | 3/2007 |
| WO | WO 2008/027218 A2 | 3/2008 |

OTHER PUBLICATIONS

U.S. Appl. No. 11/773,352, filed Jul. 3, 2007, Smith.
U.S. Appl. No. 11/929,451, filed Oct. 30, 2007, Kogure et al.
U.S. Appl. No. 60/627,952, filed Nov. 16, 2004, Matsumura et al.
U.S. Appl. No. 60/775,361, filed Dec. 29, 2005, Reed et al.
Anonymous, "What is the Difference between Liposomes and Transfersomes?" URL= http://www.idea-ag.de/web/en/faq/index_text.html, pp. 1-3, retrieved Sep. 12, 2007
Baboota et al., "Cyclodetrins in Drug Delivery Systems: An update" Pharma Articles, NET, 2003; http://www.pharmainfo.net/eclusive/reviews/cyclodetrins_in_drug_delivery_systems:_an_update/.
Bajaj et al., "Current Trends in Novel Drug Delivery Systems," URL: http://www.expresspharmaonline.com/20041202/bangladeshpharmasector09.shtml, retrieved Aug. 23, 2007, 3 pages.
Barbu et al., "Polymeric Materials for Ophthalmic Drug Delivery: Trends and Perspectives," *Journal of Materials Chemistry*, 16:3439-3443, 2006.
Benson, "Transdermal Drug Delivery: Penetration Enhancement Techniques," *Current Drug Delivery*, 2:23-33, 2005.
Cevc, "Drug delivery across the skin," *Expert Opinion on Investigational Drugs* 6(12) Abstract 1997.
Challa et al., "Cyclodextrins in drug delivery: an updated review," *AAPS PharmSciTech* 6(2):E329-57, Oct. 14, 2005.
Chembytes e-zine, "The Birth of new Delivery Systems" Article (1999) http://www.chemsoc.org/chembytes/ezine/1999/berressem.htm.
Conacher et al., *Niosomes as Immunological Adjuvants*, in "Synthetic Surfactant Vesicles" (Ed. I.F. Uchegbu) International Publishers Distributors Ltd. Singapore, 2000 pp. 185-205.
Cross et al., "Physical Enhancement of Transdermal Drug Application: Is Delivery Technology Keeping up with Pharmaceutical Development?," *Current Drug Delivery*, 1:81-92, 2004.
Davaran et al., "Synthesis and Characterization of Methacrylic Derivatives of 5-Amino Salicylic Acid with pH-sensitive Swelling Properties," *AAPS PharmSciTech* 2(4):29, Dec. 3, 2001.
Fu et al., "Biomedical Applications of Gold Nanoparticles Functionalized Using Hetero-Bifunctional Poly(ethyleneglycol) Spacer," *Materials Research Society Symposium Proceedings* 845:AA5.4.1-AA5.4.6, 2005.
Gennaro (editor), "Remington: The Science and Practice of Pharmacy" 19th ed., Lippincott Williams & Wilkins, Baltimore MD, 1995.
Grimnes; "Pathways of Ionic Flow Through Human Skin in vivo," *Acta Dermato-Venereologica* 64(2):93-98, 1984.
Honeywell-Nguyen et al., "Vesicles as a tool for Transdermal and Dermal Delivery," *Drug Discovery Today: Technologies* 2(1):67-74, 2005.
Jain et al., "Transfersomes—a novel vesicular carrier for enhanced transdermal delivery: development, characterization, and performance evaluation," *Drug Development and Industrial Pharmacy* 29(9):1013-26, 2003.
Kumar et al., "Lecithin Organogels as a Potential Phospholipid-structured System for Topical Drug Delivery: a Review," *AAPS PharmSciTech* 6(2):E298-310, Oct. 6, 2005.
Kwon et al., "Electrically Erodible Polymer Gel for Controlled Release of Drugs," *Nature* 354(6351):291-3, Nov. 28, 1991.
Loyd, "The History of Pluronic Lecithin Organogel: An Interview With Marty Jones, BSPharm, FACA, FIACP," *International Journal of Pharmaceutical Compounding* 7(3):180 -83, May/Jun. 2003.
Loyd, "Selegiline Hydrochloride 10 mg/mL in Pluronic Lecithin Organogel," *International Journal of Pharmaceutical Compounding* 8(1):59, Jan./Feb. 2004.
Malone et al., "Freeform Fabrication of Electroactive Polymer Actuators and Electromechanical Devices," *Proceedings of the 15th Solid Freeform Fabrication Symposium*, Austin TX, Aug. 2004, pp. 697-708.
Merclin et al. "Iontophoretic delivery of 5-aminolevulinic acid and its methyl ester using a carbopol gel as vehicle," *Journal of Controlled Release* 98(1):57-65, 2004.
Mohomed, K., et al., "Persistent Interactions Between Hydroxylated Nanoballs and Atactic poly(2-Hydroxyethyl Methacrylate) (PHEMA)," *Chemical Communications*, pp. 3277-3279, 2005.
Monfardini et al., "Stabilization of substances in circulation," *Bioconjugate Chemistry* 9(4):418-450, Jul.-Aug. 1998.
Murdan, "A Review of Pluronic Lecithin Organogel as a Topical and Transdermal Drug Delivery System," *Hospital Pharmacist* 12:267-270, 2005.
Nasseri et al., "Lecithin—Stabilized Microemulsion—Based Oranogels for Topical Application of Ketorolac Tromethamine. II. In Vitro Release Study," *Iranian Journal of Pharmaceutical Research* 2(2):pp. 117-123, Spring 2003.
Okumus et al., "Vesicle Encapsulation Studies Reveal that Single Molecule Ribozyme Heterogeneities Are Intrinsic," *Biophysical Journal* 87:2798-2806, Oct. 2004.
Persing et al. "Taking toll: lipid A mimetics as adjuvants and immunomodulators," *Trends in Microbiology* 10(10 Suppl.):S32-S37, 2002.
Sahota et al., "Physical Characterization of Polymer Electrolytes as Novel Iontophoretic Drug Delivery Devices," *Drug Development and Industrial Pharmacy* 25(3):307-13, Mar. 1999.
Sahota et al., "In Vitro Iontophoretic Release of Lithium Chloride and Lidocaine Hydrochloride from Polymer Electrolytes," *Drug Development and Industrial Pharmacy* 26(10):1039.
Sastry et al., "New approaches to the synthesis of anisotropic, core-shell and hollow metal nanostructures," *Journal of Materials Chemistry* 15:3161-3174, 2005.
Segura et al., "Crosslinked Hyaluronic Acid Hydrogels: a Strategy to Functionalize and Pattern," *Biomaterials* 26(4):359-71, Feb. 2005.
Sihorkar et al., "Polysaccharide coated niosomes for oral drug delivery: formulation and in vitro stability studies," *Pharmazie* 55(2):107-113, Feb. 2000.
Szejtli et al., "Past, Present, and Future of Cyclodextrin Research," *Pure and Applied Chemistry* 76(10):1825-1845, 2004.
Tapash et al., "Transdermal and Topical Drug Delivery Systems" Interpharm Press, Inc., Englewood, CO, 1997.
Thomas et al., "Photochemistry of chromophore-functionalized gold nanoparticles," *Pure and Applied Chemistry* 74(9):1731-1738, 2002.
Uchida et al., "Introduction of poly-L-lactic acid microspheres into the skin using supersonic flow: effects of helium gas pressure, particle size and microparticle dose on the amount introduced into hairless rat skin," *Journal of Pharmacy and Pharmacology* 54(6):781-90, Jun. 2002.
Wei et al. "Separation and determination of norepinephrine, epinephrine and isoprinaline enantiomers by capillary electrophoresis in pharmaceutical formulation and human serum," *Journal of Chromatography A* 1098(1-2):166-71, Dec. 9, 2005.
Xu et al., "Synthesis and Characterization of Well-Defined Poly(2-hydroxyethyl methacrylate-co-styrene)-graft-poly(epsilon-caprolactone) by Sequential Controlled Polymerization," *Journal of Polymer Science Part A Polymer Chemistry* 42(21), pp. 5523-5529, 2004.
Yadavalli et al., "Microfabricated Protein-containing Poly(ethylene glycol) Hydrogel Arrays for Biosensing," *Sensors and Actuators B* 97:290-297, 2004.
Yoshida et al., "Structure-Transport Relationships in Transdermal Iontophoresis," *Advanced Drug Delivery Reviews* 9:239-264, 1992.
Cabovska, "Investigations of Separation Mechanisms in Capillary Electrophoresis and High Performance Liquid Chromatography," Proquest, UMI No. 3120882, 2004.
Fleisher, D., et al., "Topical delivery of growth hormone releasing peptide using liposomal systems: an in vitro study using hairless mouse skin," *Life Sci.* 57(13):1293-7, 1995.
Krämer, S., "Absorption Prediction from Physiochemical Parameters," *Pharm Sci Technolo Today*, 2(9):373-380, Sep. 1999.
Recchia, J., et al., "A Semisynthetic Quillaja Saponin as a Drug Delivery Agent for Aminoglycoside Antibiotics," *Pharmaceut. Res.*, 12(12):1917-1923 (1995).
Zhao, H., "Synthesis and Enzymatic Resolution of Amino Acid Esters in "Green" Solvents—Ionic Liquids," Dissertation, New Jersey Institute of Technology, Aug. 2002, 141 pages.

\* cited by examiner

IONTOPHORETIC SYSTEMS, DEVICES, AND METHODS OF DELIVERY OF ACTIVE AGENTS TO BIOLOGICAL INTERFACE

CROSS-REFERENCE TO RELATED APPLICATION

This application claims the benefit under 35 U.S.C. §119 (e) of U.S. Provisional Patent Application No. 60/755,391, filed Dec. 30, 2005, which application is incorporated herein by reference in its entirety.

BACKGROUND

1. Field

This disclosure generally relates to the field of iontophoresis and, more particularly, to the delivery of active agents such as therapeutic agents or drugs to a biological interface under the influence of electromotive force and/or current.

2. Description of the Related Art

Iontophoresis employs an electromotive force and/or current to transfer an active agent such as an ionic drug or other therapeutic agent to a biological interface, for example skin or mucus membrane.

Iontophoresis devices typically include an active electrode assembly and a counter electrode assembly, each coupled to opposite poles or terminals of a voltage source, for example a chemical battery or an external power station connect to the iontophoresis devices via electrical leads. Each electrode assembly typically includes a respective electrode element to apply an electromotive force and/or current. Such electrode elements often comprise a sacrificial element or compound, for example silver or silver chloride.

The active agent may be either cationic or anionic, and the voltage source can be configured to apply the appropriate voltage polarity based on the polarity of the active agent. Iontophoresis may be advantageously used to enhance or control the delivery rate of the active agent. The active agent may be stored in a reservoir such as a cavity. Alternatively, the active agent may be stored in a reservoir such as a porous structure or a gel.

An ion selective membrane may be positioned to serve as a polarity selective barrier between the active agent reservoir and the biological interface. The membrane, typically substantially only permeable with respect to one particular type of ions (e.g., a charged active agent), prevents the back flux of the oppositely charged ions from the skin or mucous membrane. Although combining membranes in layers with iontophoresis results in efficient, controlled delivery of the active agents and allows for flexibility in choosing the electrode system, delivery from these membranes may be difficult. Because the biologically active agent, such as a drug or vaccine, may have to be deposited on the membrane in dry form, the amount of drug absorbed thereon may not be sufficient to meet the dosage requirement.

Commercial acceptance of iontophoresis devices is dependent on a variety of factors, such as cost to manufacture, shelf life, stability during storage, efficiency and/or timeliness of active agent delivery, biological capability, and/or disposal issues. Commercial acceptance of iontophoresis devices is also dependent on their ease-of-use and versatility, as well as their ability to provide effective and controlled delivery of biologically active agents. Therefore, it may be desirable to have novel approaches for providing controlled delivery of active agents using iontophoresis devices.

The present disclosure is directed to overcome one or more of the shortcomings set forth above, and provide further related advantages.

BRIEF SUMMARY

In one embodiment, the present disclosure is directed to a transdermal delivery device to passively deliver active agents to a biological interface, comprising: an active agent reservoir comprising a first active agent of a first polarity; an outer active agent membrane comprising a second active agent of the first polarity distributed therein, the outer active agent membrane taking the form of an ion-exchange membrane of a second polarity; and an interfacial layer having a first side adjacent to the outer active agent membrane and a second side configured to contact a biological interface, the interfacial layer comprising a plurality of freely diffusible monovalent co-ions of the first polarity.

In one aspect, the present disclosure is directed to an iontophoresis device to delivery active agents to a biological interface. The iontophoresis device includes an active electrode element, an electrolyte reservoir, an outer active agent membrane, and an interfacial layer.

The active electrode element is operable to provide an electrical potential. The electrolyte reservoir includes an electrolyte composition. The outer active agent membrane includes a number of pores. In some embodiments, a cross-linked polyelectrolyte gel is distributed in the pores. In some further embodiments, a first positively charged active agent is distributed in the cross-linked polyelectrolyte gel.

The interfacial layer may include a first side adjacent to the outer active agent membrane and a second side configured to contact a biological interface. In some embodiments, the interfacial layer includes a plurality of monovalent ions having a positive charge.

In another aspect, the present disclosure is directed to a transdermal delivery device to deliver active agents to a biological interface. The device includes an active agent reservoir, an outer active agent membrane, and an interfacial layer.

The active agent reservoir includes a first active agent of a first polarity. The outer active agent membrane includes a number of pores. In some embodiments, a cross-linked polyelectrolyte gel is distributed in the pores. In some embodiments, a second active agent of the first polarity is distributed in the cross-linked polyelectrolyte gel. The interfacial layer includes a first side adjacent to the outer active agent membrane and a second side configured to contact a biological interface. In some embodiments, the interfacial layer includes a plurality of monovalent ions of the first polarity.

In another aspect, the present disclosure is directed to an iontophoresis device is provided for the delivery of active agents to a biological interface such as skin or mucous membranes which may improve the availability, stability, loading and release of active agent. The device includes an active electrode element operable to provide an electrical potential; an electrolyte reservoir comprising an electrolyte composition; and an outer active agent membrane comprising a polyelectrolyte gel matrix within a microporous membrane. In some embodiments, the polyelectrolyte gel matrix takes the form of a cross-linked polyelectrolyte gel matrix. The outer active agent membrane may be an integral component of the iontophoretic device or may be stored separately and positioned on the outer surface of the device before use. Optionally, an inner ion selective membrane may be positioned between the electrolyte reservoir and the outer active agent membrane; and an inner active agent reservoir may be positioned between the inner ion selective membrane and the outer active agent membrane. Optionally an outer ion selective membrane may be positioned between the inner drug reservoir and the outer active agent membrane.

The cation-exchange cross-linked polyelectrolyte gel filling the pores of the microporous membrane binds a cationic active agent, thereby enhancing the loading capacity. Due to the electrochemically induced pH shift which causes protons to migrate to the inner active agent reservoir, the negatively charged polyelectrolyte gel is neutralized and the cationic active agent dissociates from the gel matrix.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
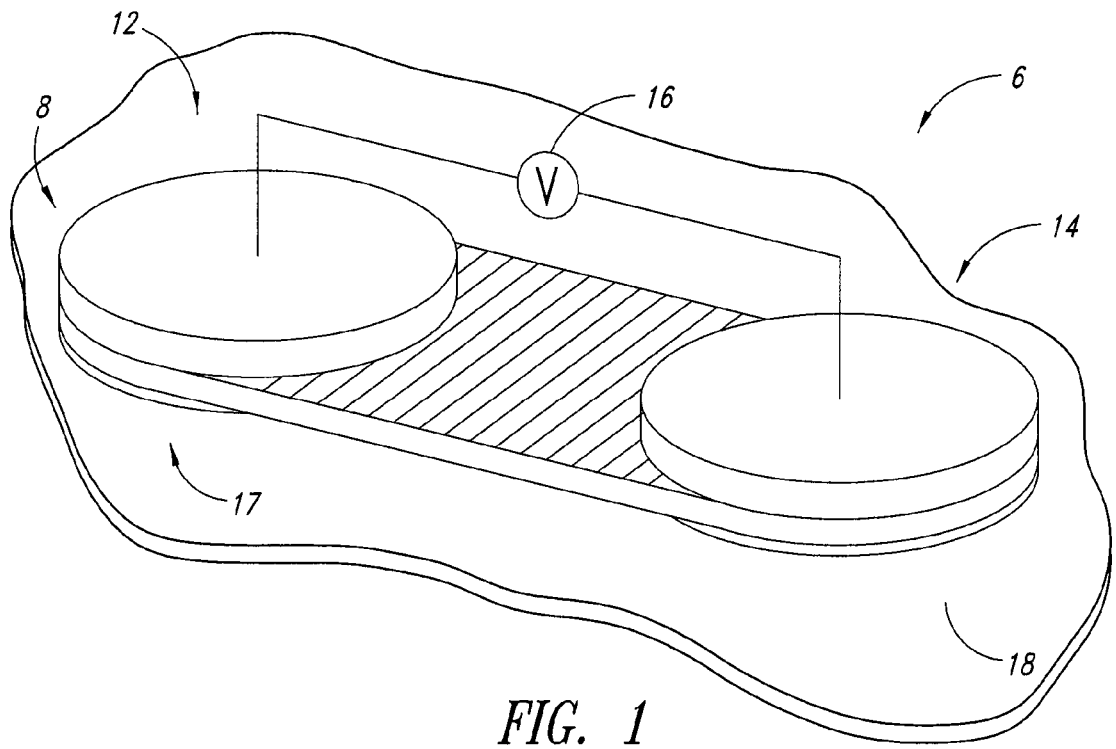
FIG. 1 is a top front view of an iontophoretic drug delivery system according to one illustrated embodiment.

In the following description, certain specific details are set forth in order to provide a thorough understanding of various disclosed embodiments. One skilled in the relevant art, however, will recognize that embodiments may be practiced without one or more of these specific details, or with other methods, components, materials, etc. In other instances, well-known structures associated with controllers including but not limited to voltage and/or current regulators have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment," or "in another embodiment" means that a particular referent feature, structure, or characteristic described in connection with the embodiment is included in at least one embodiment. Thus, the appearances of the phrases "in one embodiment" or "in an embodiment," or "in another embodiment" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to an iontophoresis device including an "active agent membrane" includes a single active agent membrane, or two or more active agent membranes. It should also be noted that the term "or" is generally employed in its sense including "and/or" unless the content clearly dictates otherwise.

As used herein the term "membrane" means a boundary, a layer, barrier, or material, which may, or may not be permeable. The term "membrane" may further refer to an interface. Unless specified otherwise, membranes may take the form a solid, liquid, or gel, and may or may not have a distinct lattice, non cross-linked structure, or cross-linked structure.

As used herein the term "ion selective membrane" means a membrane that is substantially selective to ions, passing certain ions while blocking passage of other ions. An ion selective membrane, for example, may take the form of a charge selective membrane, or may take the form of a semi-permeable membrane.

As used herein the term "charge selective membrane" means a membrane that substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane. A cation exchange membrane substantially permits the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane substantially permits the passage of anions and substantially blocks cations. Examples of commercially available anion exchange membranes include those available under the designators NEOSEPTA, AM-1, AM-3, AMX, AHA, ACH, and ACS also from Tokuyama Co., Ltd.

As used herein and in the claims, the term "bipolar membrane" means a membrane that is selective to two different charges or polarities. Unless specified otherwise, a bipolar membrane may take the form of a unitary membrane structure, a multiple membrane structure, or a laminate. The unitary membrane structure may include a first portion including cation ion exchange materials or groups and a second portion opposed to the first portion, including anion ion exchange materials or groups. The multiple membrane structure (e.g., two film structure) may include a cation exchange membrane laminated or otherwise coupled to an anion exchange membrane. The cation and anion exchange membranes initially start as distinct structures, and may or may not retain their distinctiveness in the structure of the resulting bipolar membrane.

As used herein and in the claims, the term "semi-permeable membrane" means a membrane that is substantially selective based on a size or molecular weight of the ion. Thus, a semi-permeable membrane substantially passes ions of a first molecular weight or size, while substantially blocking passage of ions of a second molecular weight or size, greater than the first molecular weight or size. In some embodiments, a semi-permeable membrane may permit the passage of some molecules at a first rate, and some other molecules at a second rate different from the first. In yet further embodiments, the "semi-permeable membrane" may take the form of a selectively permeable membrane allowing only certain selective molecules to pass through it.

As used herein and in the claims, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "gel matrix" means a type of reservoir, which takes the form of a three dimensional network, a colloidal suspension of a liquid in a solid, a semi-solid, a cross-linked gel, a non cross-linked gel, a jelly-like state, and the like. In some embodiments, the gel matrix may result from a three dimensional network of entangled macromolecules (e.g., cylindrical micelles). In some embodiments, a gel matrix may include hydrogels, organogels, and the like. The term "hydrogel" refers to three-dimensional network of, for example, cross-linked hydrophilic polymers in the form of a gel and substantially composed of water. Hydrogels may have a net positive or negative charge, or may be neutral.

Various electrically conductive hydrogels, for example, have been known and used in the medical field to provide an electrical interface to the skin of a subject or within a device to couple electrical stimulus into the subject. Hydrogels hydrate the skin, thus protecting against burning due to electrical stimulation through the hydrogel, while swelling the skin and allowing more efficient transfer of an active component. Examples of such hydrogels are disclosed in U.S. Pat. Nos. 6,803,420; 6,576,712; 6,908,681; 6,596,401; 6,329,488; 6,197,324; 5,290,585; 6,797,276; 5,800,685; 5,660,178; 5,573,668; 5,536,768; 5,489,624; 5,362,420; 5,338,490; and 5,240995, herein incorporated in their entirety by reference. Further examples of such hydrogels are disclosed in U.S. Patent applications 2004/166147; 2004/105834; and 2004/247655, herein incorporated in their entirety by reference. Product brand names of various hydrogels and hydrogel sheets include Corplex™ by Corium, Tegagel™ by 3M, Pura-Matrix™ by BD; Vigilon™ by Bard; ClearSite™ by Conmed Corporation; FlexiGel™ by Smith & Nephew; Derma-Gel™ by Medline; Nu-Gel™ by Johnson & Johnson; and Curagel™ by Kendall, or acrylhydrogel films available from Sun Contact Lens Co., Ltd.

As used herein and in the claims, the term "functional group" generally refers to a chemical group that confers special properties or particular functions to an article (e.g., a surface, a molecule, a substance, a particle, nanoparticle, and the like). Among the chemical groups, examples include an atom, an arrangement of atoms, an associated group of atoms, molecules, moieties, and that like, that confer certain characteristic properties on the article comprising the functional groups. Exemplary characteristic properties and/or functions include chemical properties, chemically reactive properties, association properties, electrostatic interaction properties, bonding properties, biocompatible properties, and the like. In some embodiments, the functional groups include one or more nonpolar, hydrophilic, hydrophobic, organophilic, lipophilic, lipophobic, acidic, basic, neutral, functional groups, and the like.

As used herein and in the claims, the term "polyelectrolyte," or "polyelectrolytes" refers to polymers comprising repeating units that include an electrolyte group. Exemplary electrolyte groups include functional groups (e.g. charge functional groups, and the like), as well as active group such as, for example, cations, anions, amines, substituted amino groups, acids, halocarbons, sulfonic acids, carboxylics, phenols, quaternary amines, metals, $—NH_3^+$, $—COOH$, $—COO^-$, $—SO_3$, $—CH_2N^+(CH_3)_3$, and the like, or combinations thereof. In some embodiments, charge functional groups are capable of maintaining either a positive or negative charge over a broad range of environments (e.g., varying pH range). In some embodiments, ionic constituents of a first polarity are attached to the "polyelectrolyte" polymer chain while those of a second polarity, opposite to the first, are free to diffuse into a solution. In some embodiments, the second polarity groups will dissociate in aqueous solutions, making the polymers charged.

In some embodiments, polyelectrolytes may have properties similar to both electrolytes (salts) and polymers (high molecular weight compounds), and may be referred to as polysalts. Like salts, polyelectrolytes solutions are electrically conductive, and like polymers, polyelectrolytes solutions take the form of viscous mixtures. Examples of polyelectrolytes include biological molecules such as, for example, polypeptides (e.g., all proteins), deoxyribonucleic acids (DNAs), and the like.

Further examples of polyelectrolytes include weak or strong polyelectrolytes, natural and synthetic polyelectrolytes, charged polymers, polypeptides, 2-hydroxyethyl methacrylates, poly(ethylene glycol) methacrylates, poly(sodium polystyrene sulfonate), poly(acrylic acid), poly(styrene sulphonate), poly(ethyleneimine), poly(acryloyl-L-proline methyl ester), poly(dimethylaminopropylacrylamides), and salts thereof.

As used herein and in the claims, the term "polyelectrolyte gel," or "polyelectrolyte gel matrix" refers to a "gel matrix" including ionic constituents (e.g., cationic, anionic, and the like). In some embodiments, the "polyelectrolyte gel" comprises one or more polyelectrolytes. In some embodiments, the "polyelectrolyte gel" comprises ionic constituents that form part on an ionic network.

In some embodiments, the "polyelectrolyte gel" forms a "gel matrix" suitable for filling pores of, for example, porous and/or microporous membranes, substrates, and the like. In some further embodiments, the "polyelectrolyte gel" may form a cross-linked "gel matrix" suitable for filling pores of porous and/or microporous membranes, substrates, and the like. Examples of polyelectrolyte gels include ion-exchange resins, hydrogels, and the like.

In one embodiment, the polyelectrolyte gels comprise a polyelectrolyte hydrogel. In another embodiment the polyelectrolyte gels may take the form of a three-dimensional network of cross-linked hydrophilic polymers in the form of a gel and substantially composed of water. Polyelectrolyte hydrogels may have a net negative or net positive charge, or may be neutral. Certain details of porous gels and porous polyelectrolyte gels are disclosed in U.S. Pat. No. 6,258,276, issued Jul. 10, 2001; U.S. patent application Ser. No. 09/284,650, filed Oct. 17, 1997, having U.S. Publication No. 2003/0168404; U.S. patent application Ser. No. 10/769,953, filed Feb. 2, 2004, having U.S. Publication No. 2004/0203149; U.S. patent application Ser. No. 10/484,059, filed Jul. 18, 2002, having U.S. Publication No. 2005/0011826; PCT Application No. PCT/CA97/00770, filed Oct. 17, 1997, having PCT Publication No. WO 98/17377; PCT Application No. PCT/CA2004/000120, filed Jan. 29, 2004, having PCT Publication No. WO 2004/073843; PCT Application No. PCT/CA02/01102, filed Jul. 18, 2002, having PCT Publication No. WO 03/008078 which are herein incorporated in their entirety by reference.

As used herein and in the claims, the term "reservoir" means any form of mechanism to retain an element, compound, pharmaceutical composition, active agent, and the like, in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

As used herein and in the claims, the term "active agent" refers to a compound, molecule, or treatment that elicits a biological response from any host, animal, vertebrate, or invertebrate, including for example fish, mammals, amphibians, reptiles, birds, and humans. Examples of active agents include therapeutic agents, pharmaceutical agents, pharmaceuticals (e.g., a drug, a therapeutic compound, pharmaceutical salts, and the like) non-pharmaceuticals (e.g., cosmetic substance, and the like), a vaccine, an immunological agent, a local or general anesthetic or painkiller, an antigen or a protein or peptide such as insulin, a chemotherapy agent, an anti-tumor agent.

In some embodiments, the term "active agent" further refers to the active agent, as well as its pharmacologically active salts, pharmaceutically acceptable salts, prodrugs, metabolites, analogs, and the like. In some further embodiment, the active agent includes at least one ionic, cationic, ionizeable, and/or neutral therapeutic drug and/or pharmaceutical acceptable salts thereof. In yet other embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. Other active agents may be polarized or polarizable, that is exhibiting a polarity at one portion relative to another portion. For instance, an active agent having an amino group can typically take the form an ammonium salt in solid state and dissociates into a free ammonium ion ($NH_4^+$) in an aqueous medium of appropriate pH.

The term "active agent" may also refer to electrically neutral agents, molecules, or compounds capable of being delivered via electro-osmotic flow. The electrically neutral agents are typically carried by the flow of, for example, a solvent during electrophoresis. Selection of the suitable active agents is therefore within the knowledge of one skilled in the relevant art.

In some embodiments, one or more active agents may be selected from analgesics, anesthetics, anesthetics vaccines, antibiotics, adjuvants, immunological adjuvants, immunogens, tolerogens, allergens, toll-like receptor agonists, toll-like receptor antagonists, immuno-adjuvants, immuno-modulators, immuno-response agents, immuno-stimulators, specific immuno-stimulators, non-specific immuno-stimulators, and immuno-suppressants, or combinations thereof.

Non-limiting examples of such active agents include lidocaine, articaine, and others of the caine class, morphine, hydromorphone, fentanyl, oxycodone, hydrocodone, buprenorphine, methadone, and similar opioid agonists; sumatriptan succinate, zolmitriptan, naratriptan HCl, rizatriptan benzoate, almotriptan malate, frovatriptan succinate and other 5-hydroxytryptaminel receptor subtype agonists; resiquimod, imiquidmod, and similar TLR 7 and 8 agonists and antagonists; domperidone, granisetron hydrochloride, ondansetron and such anti-emetic drugs; zolpidem tartrate and similar sleep inducing agents; L-dopa and other anti-Parkinson's medications; aripiprazole, olanzapine, quetiapine, risperidone, clozapine, and ziprasidone, as well as other neuroleptica; diabetes drugs such as exenatide; as well as peptides and proteins for treatment of obesity and other maladies.

Further non-limiting examples of active agents include ambucaine, amethocaine, isobutyl p-aminobenzoate, amolanone, amoxecaine, amylocaine, aptocaine, azacaine, bencaine, benoxinate, benzocaine, N,N-dimethylalanylbenzocaine, N,N-dimethylglycylbenzocaine, glycylbenzocaine, beta-adrenoceptor antagonists betoxycaine, bumecaine, bupivicaine, levobupivicaine, butacaine, butamben, butanilicaine, butethamine, butoxycaine, metabutoxycaine, carbizocaine, carticaine, centbucridine, cepacaine, cetacaine, chloroprocaine, cocaethylene, cocaine, pseudococaine, cyclomethycaine, dibucaine, dimethisoquin, dimethocaine, diperodon, dyclonine, ecognine, ecogonidine, ethyl aminobenzoate, etidocaine, euprocin, fenalcomine, fomocaine, heptacaine, hexacaine, hexocaine, hexylcaine, ketocaine, leucinocaine, levoxadrol, lignocaine, lotucaine, marcaine, mepivacaine, metacaine, methyl chloride, myrtecaine, naepaine, octacaine, orthocaine, oxethazaine, parenthoxycaine, pentacaine, phenacine, phenol, piperocaine, piridocaine, polidocanol, polycaine, prilocaine, pramoxine, procaine (NOVOCAINE®), hydroxyprocaine, propanocaine, proparacaine, propipocaine, propoxycaine, pyrrocaine, quatacaine, rhinocaine, risocaine, rodocaine, ropivacaine, salicyl alcohol, tetracaine, hydroxytetracaine, tolycaine, trapencaine, tricaine, trimecaine tropacocaine, zolamine, a pharmaceutically acceptable salt thereof, and mixtures thereof.

As used herein and in the claims, the term "agonist" refers to a compound that can combine with a receptor (e.g., an opioid receptor, Toll-like receptor, and the like) to produce a cellular response. An agonist may be a ligand that directly binds to the receptor. Alternatively, an agonist may combine with a receptor indirectly by forming a complex with another molecule that directly binds the receptor, or otherwise resulting in the modification of a compound so that it directly binds to the receptor.

As used herein and in the claims, the term "antagonist" refers to a compound that can combine with a receptor (e.g., an opioid receptor, a Toll-like receptor, and the like) to inhibit a cellular response. An antagonist may be a ligand that directly binds to the receptor. Alternatively, an antagonist may combine with a receptor indirectly by forming a complex with another molecule that directly binds the receptor, or otherwise results in the modification of a compound so that it directly binds to the receptor.

As used herein and in the claims, the term "effective amount" or "therapeutically effective amount" includes an amount effective at dosages and for periods of time necessary, to achieve the desired result. The effective amount of a composition containing a pharmaceutical agent may vary according to factors such as the disease state, age, gender, and weight of the subject.

As used herein and in the claims, the term "analgesic" refers to an agent that lessens, alleviates, reduces, relieves, or extinguishes a neural sensation in an area of a subject's body. In some embodiments, the neural sensation relates to pain, in other aspects the neural sensation relates to discomfort, itching, burning, irritation, tingling, "crawling," tension, temperature fluctuations (such as fever), inflammation, aching, or other neural sensations.

As used herein and in the claims, the term "anesthetic" refers to an agent that produces a reversible loss of sensation in an area of a subject's body. In some embodiments, the anesthetic is considered to be a "local anesthetic" in that it produces a loss of sensation only in one particular area of a subject's body.

As one skilled in the relevant art would recognize, some agents may act as both an analgesic and an anesthetic, depending on the circumstances and other variables including but not limited to dosage, method of delivery, medical condition or treatment, and an individual subject's genetic makeup. Additionally, agents that are typically used for other purposes may possess local anesthetic or membrane stabilizing properties under certain circumstances or under particular conditions.

As used herein and in the claims, the term "immunogen" refers to any agent that elicits an immune response. Examples of an immunogen include, but are not limited to natural or synthetic (including modified) peptides, proteins, lipids, oligonucleotides (RNA, DNA, etc.), chemicals, or other agents.

As used herein and in the claims, the term "allergen" refers to any agent that elicits an allergic response. Some examples of allergens include but are not limited to chemicals and plants, drugs (such as antibiotics, serums), foods (such as milk, wheat, eggs, etc), bacteria, viruses, other parasites, inhalants (dust, pollen, perfume, smoke), and/or physical agents (heat, light, friction, radiation). As used herein, an allergen may be an immunogen.

As used herein and in the claims, the term "adjuvant" and any derivations thereof, refers to an agent that modifies the effect of another agent while having few, if any, direct effect when given by itself. For example, an adjuvant may increase the potency or efficacy of a pharmaceutical, or an adjuvant may alter or affect an immune response.

As used herein and in the claims, the term "opioid" generally refers to any agent that binds to and/or interacts with opioid receptors. Among the opioid classes examples include endogenous opioid peptides, opium alkaloids (e.g., morphine, codeine, and the like), semi-synthetic opioids (e.g., heroin, oxycodone and the like), synthetic opioids (e.g., buprenorphinemeperidine, fentanyl, morphinan, benzomorphan derivatives, and the like), as well as opioids that have structures unrelated to the opium alkaloids (e.g., pethidine, methadone, and the like).

As used herein and in the claims, the terms "vehicle," "carrier," "pharmaceutically vehicle," "pharmaceutically carrier," "pharmaceutically acceptable vehicle," or "pharmaceutically acceptable carrier" may be used interchangeably, and refer to pharmaceutically acceptable solid or liquid, diluting or encapsulating, filling or carrying agents, which are usually employed in pharmaceutical industry for making pharmaceutical compositions. Examples of vehicles include any liquid, gel, salve, cream, solvent, diluent, fluid ointment base, vesicle, liposomes, nisomes, ethasomes, transfersomes, virosomes, non ionic surfactant vesicles, phospholipid surfactant vesicles, micelle, and the like, that is suitable for use in contacting a subject.

In some embodiments, the pharmaceutical vehicle may refer to a composition that includes and/or delivers a pharmacologically active agent, but is generally considered to be otherwise pharmacologically inactive. In some other embodiments, the pharmaceutical vehicle may have some therapeutic effect when applied to a site such as a mucous membrane or skin, by providing, for example, protection to the site of application from conditions such as injury, further injury, or exposure to elements. Accordingly, in some embodiments, the pharmaceutical vehicle may be used for protection without a pharmacological agent in the formulation.

Examples of vehicles include degradable or non-degradable polymers, hydrogels, organogels, liposomes, nisomes, ethasomes, transfersomes, virosomes, cyclic oligosaccharides, non-ionic surfactant vesicles, phospholipid surfactant vesicles, micelles, microspheres, creams, emulsions, lotions, pastes, gels, ointments, organogel, and the like, as well as any matrix that allows for transport of an agent across the skin or mucous membranes of a subject. In at least one embodiment, the vehicle allows for controlled release formulations of the compositions disclosed herein.

As used herein and in the claims, the term "subject" generally refers to any host, animal, vertebrate, or invertebrate, and includes fish, mammals, amphibians, reptiles, birds, and particularly humans.

Figure 2:
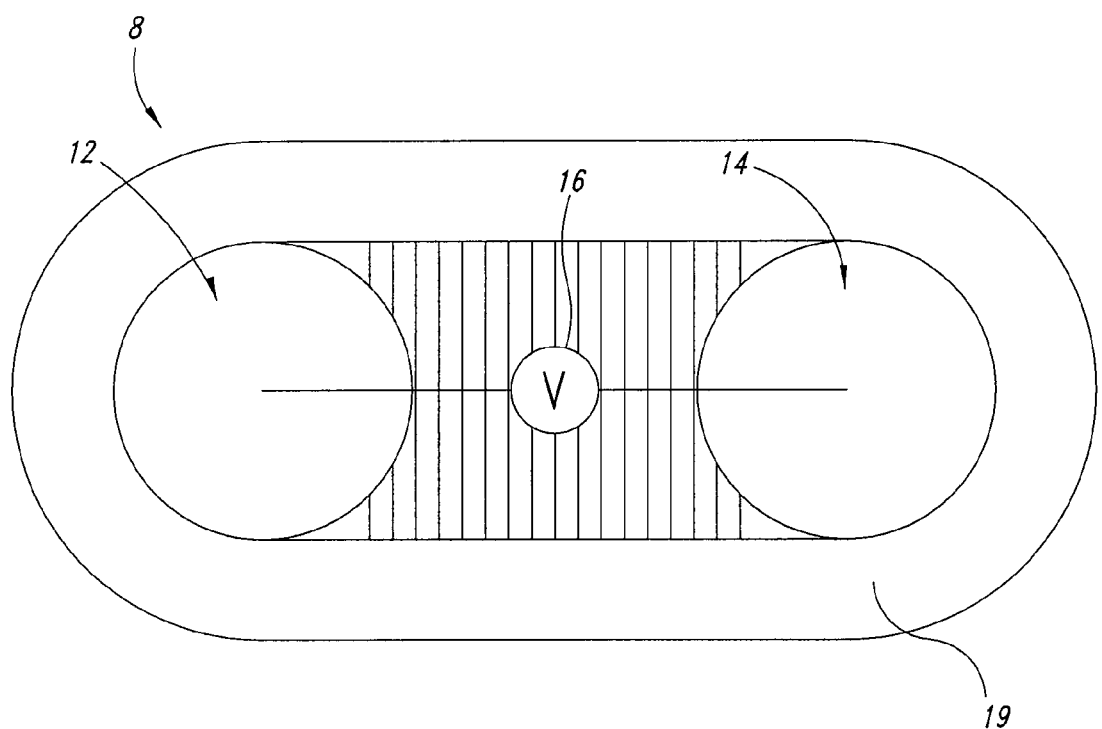
FIG. 2 is a top plan view of an iontophoretic drug delivery system according to one illustrated embodiment.

FIGS. 1 and 2 show an exemplary iontophoretic drug delivery system 6 for delivering one or more active agents to a subject. The system 6 includes an iontophoresis device 8 including active and counter electrode assemblies 12, 14, respectively, and a power source 16. The active and counter electrode assemblies 12, 14, are electrically coupleable to the power source 16 to supply an active agent contained in the active electrode assembly 12, via iontophoresis, to a biological interface 18 (e.g., a portion of skin or mucous membrane). The iontophoresis device 8 may optionally include a biocompatible backing 19. In some embodiments, the biocompatible backing 19 encases the iontophoresis devices 8. In some other embodiments, the biocompatible backing 19 physically couples the iontophoresis device 8 to the biological interface 18 of the subject. In some embodiments, the system 6 is configured for providing transdermal delivery of one or more therapeutic active agents to a biological interface of a subject and inducing analgesia or aesthesia in the subject for a limited period of time.

Figure 3:
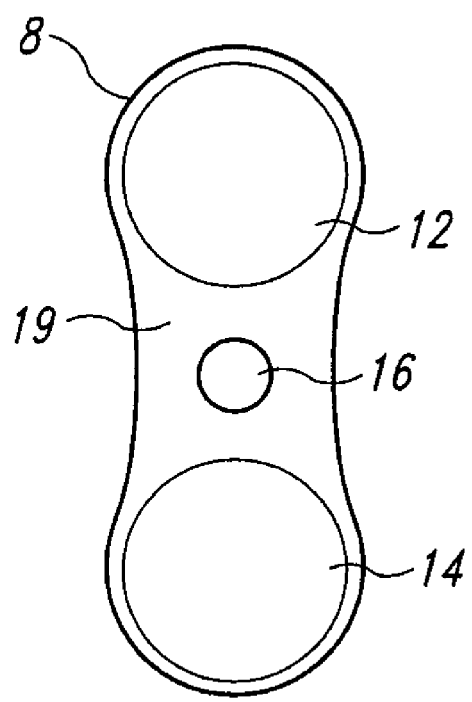
FIG. 3 is a top plan view of an iontophoretic drug delivery device comprising active and counter electrode assemblies according to one illustrated embodiment.
Figure 4:
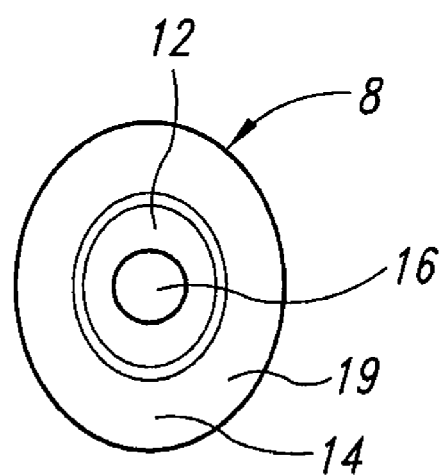
FIG. 4 is a top plan view of an iontophoretic drug delivery device comprising active and counter electrode assemblies according to another illustrated embodiment.

FIGS. 3 and 4 show exemplary transdermal delivery systems 6 for delivering of one or more active agents to a subject. The transdermal delivery systems 6 include an iontophoresis device 8 including active and counter electrode assemblies 12, 14, respectively, and a power supply system 16. The overall shape of the iontophoresis device 8 may take a variety of geometric forms including, for example, those shown in FIGS. 3 and 4.

In some embodiments, the active electrode assembly 12 takes the form of a positive electrode assembly, and the counter electrode assembly 14 as a negative electrode assembly. Alternatively, the counter electrode assembly 14 may take the form of a negative assembly, and the active electrode assembly 14 may take the form of a positive electrode assembly. The active and counter electrode assemblies 12, 14, are electrically coupleable to the power supply system 10 to supply an active agent contained in the active electrode assembly 12, via iontophoresis, to a biological interface (e.g., a portion of skin or mucous membrane).

The iontophoresis device 8 may optionally include a backing 19. In some embodiments, the backing 19 encases the iontophoresis device 8. In some other embodiments, the backing 19 physically couples the iontophoresis device 8 to a biological interface of a subject. In some embodiments, the transdermal delivery system 8 is configured to provide transdermal delivery of one or more therapeutic active agents to a biological interface of a subject.

Figure 5:
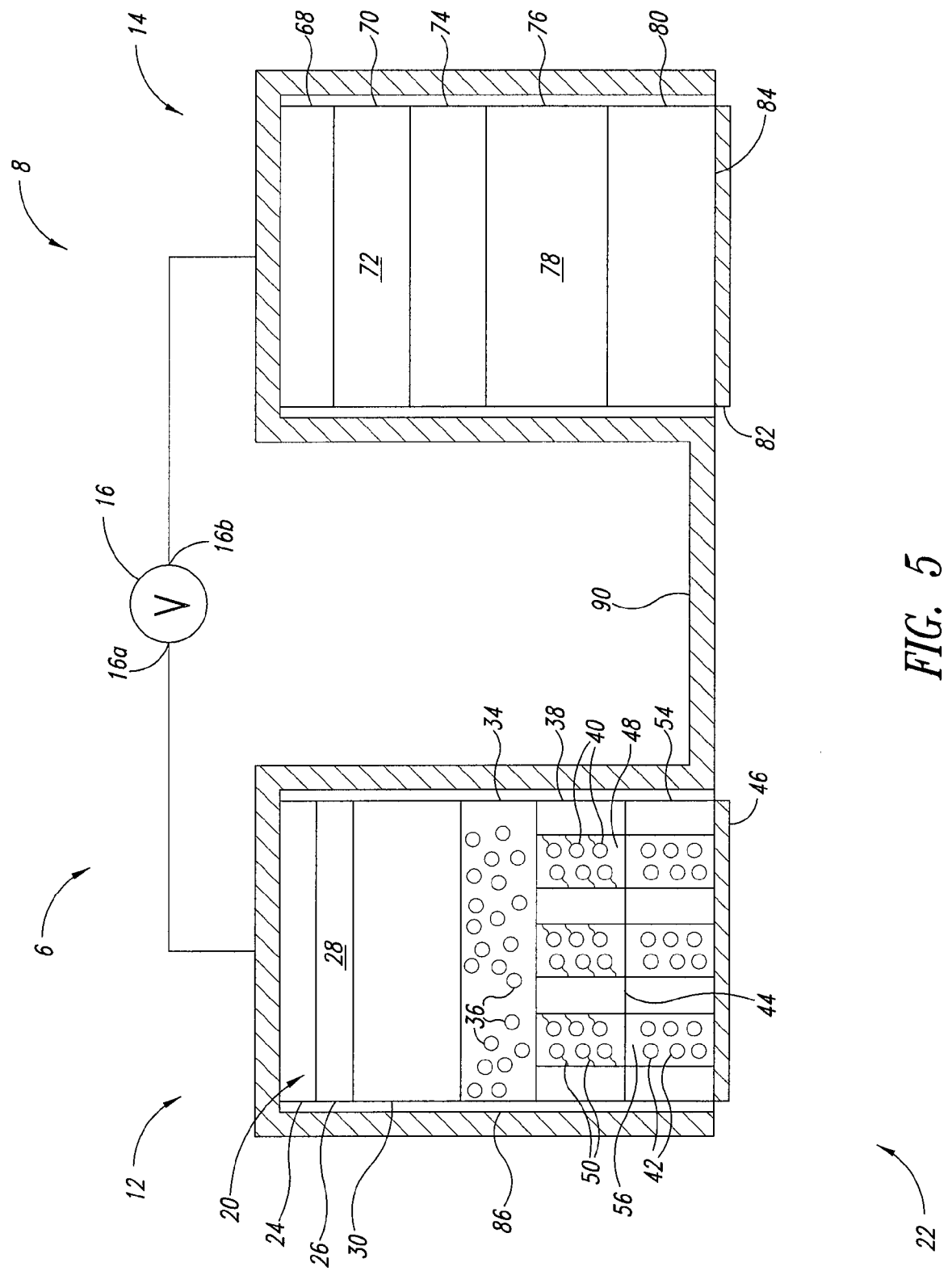
FIG. 5 is a schematic diagram of the iontophoresis device of FIGS. 1 and 2 comprising active and counter electrode assemblies according to one illustrated embodiment.
Figure 6A:
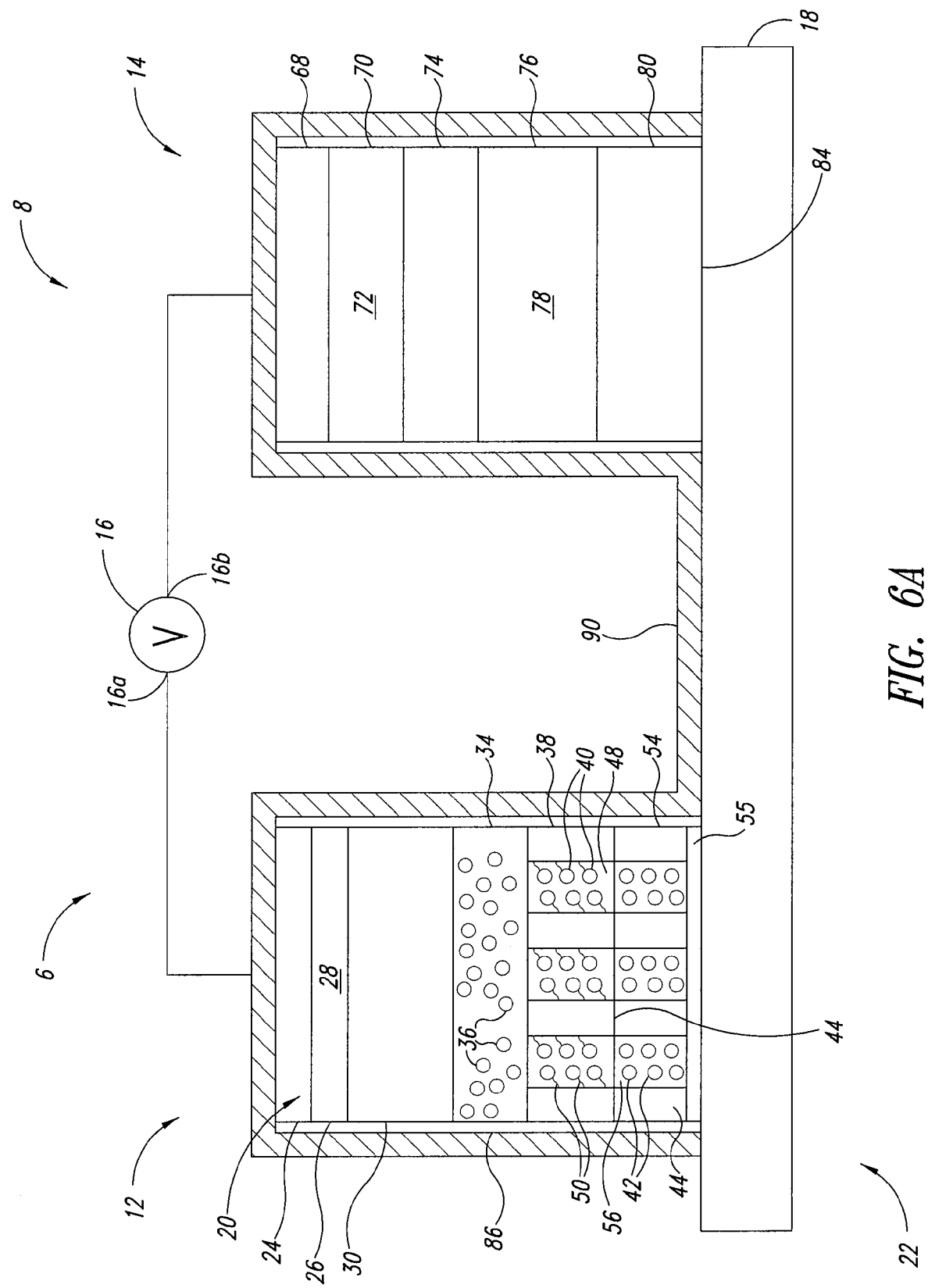
FIG. 6A is a schematic diagram of the iontophoresis device of FIG. 5 positioned on a biological interface, with an optional outer release liner removed to expose the active agent, according to another illustrated embodiment.
Figure 6B:
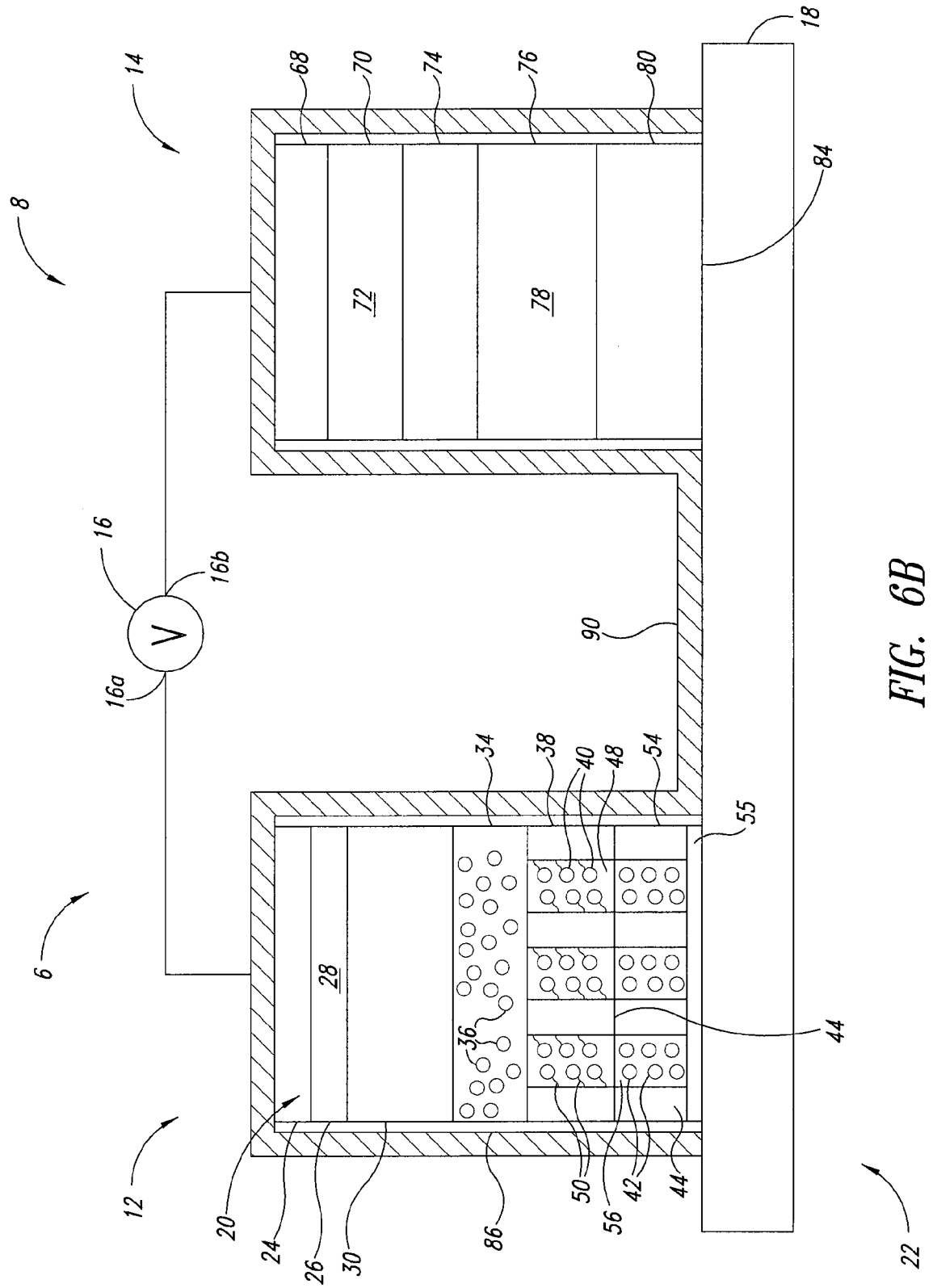
FIG. 6B is a schematic diagram of the iontophoresis device of according to another illustrated embodiment.

As shown in FIGS. 5,6A, and 6B, the active electrode assembly 12 may further comprise, from an interior 20 to an exterior 22 of the active electrode assembly 12: an active electrode element 24, an electrolyte reservoir 26 storing an electrolyte 28, an inner ion selective membrane 30, one or more inner active agent reservoirs 34, storing one or more active agents 316, an optional outermost ion selective membrane 38 that optionally caches additional active agents 40, and an optional further active agent 42 carried by an outer surface 44 of the outermost ion selective membrane 38. Each of the above elements or structures will be discussed in detail below.

The active electrode assembly 12 may comprise an optional inner sealing liner (not shown) between two layers of the active electrode assembly 12, for example, between the inner ion selective membrane 130 and the inner active agent reservoir 34. The inner sealing liner, if present, would be removed prior to application of the iontophoretic device to the biological surface 118. The active electrode assembly 12 may further comprise an optional outer release liner 46.

In some embodiments, the one or more active agent reservoirs 34 are loadable with a vehicle and/or pharmaceutical composition for transporting, delivering, encapsulating, and/or carrying the one or more active agents 36, 40, 42. In some embodiments, the pharmaceutical composition includes a therapeutically effective one or more active agents 36, 40, 42. The active electrode element 24 is electrically coupled to a first pole 16a of the power source 16 and positioned in the active electrode assembly 12 to apply an electromotive force to transport the active agent 36, 40, 42 via various other components of the active electrode assembly 12. Under ordinary use conditions, the magnitude of the applied electromotive force is generally that required to deliver the one or more active agents according to a therapeutic effective dosage protocol. In some embodiments, the magnitude is selected such that it meets or exceeds the ordinary use operating electrochemical potential of the iontophoresis delivery device 8. The at least one active electrode element 24 is operable to provide an electromotive force for driving the pharmaceutical composition (comprising the at least one analgesic or anesthetic active agent in combination with the at least one opioid antagonist) for inducing analgesia or anesthesia in the subject from the at least one active agent reservoir 34, to the biological interface 18 of the subject.

The active electrode element 24 may take a variety of forms. In one embodiment, the active electrode element 24 may advantageously take the form of a carbon-based active electrode element. Such may, for example, comprise multiple layers, for example a polymer matrix comprising carbon and a conductive sheet comprising carbon fiber or carbon fiber paper, such as that described in commonly assigned pending Japanese patent application 2004/317317, filed Oct. 29, 2004. The carbon-based electrodes are inert electrodes in that they do not themselves undergo or participate in electrochemical reactions. Thus, an inert electrode distributes current through the oxidation or reduction of a chemical species capable of accepting or donating an electron at the potential applied to the system, (e.g., generating ions by either reduction or oxidation of water). Additional examples of inert electrodes include stainless steel, gold, platinum, capacitive carbon, or graphite.

Alternatively, an active electrode of sacrificial conductive material, such as a chemical compound or amalgam, may also be used. A sacrificial electrode does not cause electrolysis of water, but would itself be oxidized or reduced. Typically, for an anode a metal/metal salt may be employed. In such case, the metal would oxidize to metal ions, which would then be precipitated as an insoluble salt. An example of such anode includes an Ag/AgCl electrode. The reverse reaction takes place at the cathode in which the metal ion is reduced and the corresponding anion is released from the surface of the electrode.

Where a sacrificial electrode (e.g., Ag/AgCl) is employed as the anode, the electrode itself is oxidized. Because no proton is produced electrochemically, the electrolyte 28 may be maintained as acidic by a buffer solution. Under the electrical field, a portion of the $H^+$ ions in the electrolyte reservoir can be induced to migrate to the inner active agent reservoir 34.

The electrolyte reservoir 26 may take a variety of forms including any structure capable of retaining electrolyte 28, and in some embodiments may even be the electrolyte 28 itself, for example, where the electrolyte 28 is in a gel, semisolid or solid form. For example, the electrolyte reservoir 26 may take the form of a pouch or other receptacle, a membrane with pores, cavities, or interstices, particularly where the electrolyte 28 is a liquid.

In one embodiment, the electrolyte 28 comprises ionic or ionizable components in an aqueous medium, which can act to conduct current towards or away from the active electrode element. Suitable electrolytes include, for example, aqueous solutions of salts. Preferably, the electrolyte 28 includes salts of physiological ions, such as, sodium, potassium, chloride, and phosphate. In some embodiments, the one or more electrolyte reservoirs 24 including an electrolyte 28 comprising at least one biologically compatible anti-oxidant selected from ascorbate, fumarate, lactate, and malate, or salts thereof.

Once an electrical potential is applied, when an inert electrode element is in use, water is electrolyzed at both the active and counter electrode assemblies. In certain embodiments, such as when the active electrode assembly is an anode, water is oxidized. As a result, oxygen is removed from water while protons ($H^+$) are produced. In one embodiment, the electrolyte 28 may further comprise an anti-oxidant. In some embodiments, the anti-oxidant is selected from anti-oxidants that have a lower potential than that of, for example, water. In such embodiments, the selected anti-oxidant is consumed rather than having the hydrolysis of water occur. In some further embodiments, an oxidized form of the anti-oxidant is used at the cathode and a reduced form of the anti-oxidant is used at the anode. Examples of biologically compatible anti-oxidants include, but are not limited to, ascorbic acid (vitamin C), tocopherol (vitamin E), or sodium citrate.

As noted above, the electrolyte 28 may take the form of an aqueous solution housed within a reservoir 26, or in the form of a dispersion in a hydrogel or hydrophilic polymer capable of retaining substantial a amount of water. For instance, a suitable electrolyte may take the form of a solution of 0.5 M disodium fumarate: 0.5 M polyacrylic acid: 0.15 M anti-oxidant.

The inner ion selective membrane 30 is generally positioned to separate the electrolyte 28 and the inner active agent reservoir 34, if such a membrane is included within the device. The inner ion selective membrane 30 may take the form of a charge selective membrane. For example, when the active agent 36, 40, 42 comprises a cationic active agent, the inner ion selective membrane 30 may take the form of an anion exchange membrane, selective to substantially pass anions and substantially block cations. The inner ion selective membrane 30 may advantageously prevent transfer of undesirable elements or compounds between the electrolyte 28 and the inner active agent reservoir 34. For example, the inner ion selective membrane 30 may prevent or inhibit the transfer of sodium ($Na^+$) ions from the electrolyte 28, thereby increasing the transfer rate and/or biological compatibility of the iontophoresis device 8.

The inner active agent reservoir 34 is generally positioned between the inner ion selective membrane 30 and the outermost ion selective membrane 38. The inner active agent reservoir 34 may take a variety of forms including any structure capable of temporarily retaining active agent 36. For example, the inner active agent reservoir 34 may take the form of a pouch or other receptacle, a membrane with pores, cavities, or interstices, particularly where the active agent 36 is a liquid. The inner active agent reservoir 34 further may comprise a gel matrix.

Optionally, an outermost ion selective membrane 38 is positioned generally opposed across the active electrode assembly 12 from the active electrode element 24. The outermost membrane 38 may, as in the embodiment illustrated in FIGS. 5, 6A, and 6B, take the form of an ion exchange membrane having pores 48 (only one called out in FIGS. 5, 6A, and 6B for sake of clarity of illustration) of the ion selective membrane 38 including ion exchange material or groups 50 (only three called out in FIGS. 5, 6A, and 6B for sake of clarity of illustration). Under the influence of an electromotive force or current, the ion exchange material or groups 50 selectively substantially passes ions of the same polarity as active agent 36, 40, while substantially blocking ions of the opposite polarity. Thus, the outermost ion exchange membrane 38 is charge selective. Where the active agent 36, 40, 42 is a cation (e.g., lidocaine), the outermost ion selective membrane 38 may take the form of a cation exchange membrane, thus allowing the passage of the cationic active agent while blocking the back flux of the anions present in the biological interface, such as skin.

The outermost ion selective membrane 38 may optionally cache active agent 40. Without being limited by theory, the ion exchange groups or material 50 temporarily retains ions of the same polarity as the polarity of the active agent in the absence of electromotive force or current and substantially releases those ions when replaced with substitutive ions of like polarity or charge under the influence of an electromotive force or current.

Alternatively, the outermost ion selective membrane 38 may take the form of semi-permeable or microporous membrane which is selective by size. In some embodiments, such a semi-permeable membrane may advantageously cache active agent 40, for example by employing the removably releasable outer release liner to retain the active agent 40 until the outer release liner is removed prior to use.

The outermost ion selective membrane 38 may be optionally preloaded with the additional active agent 40, such as ionized or ionizable drugs or therapeutic agents and/or polarized or polarizable drugs or therapeutic agents. Where the outermost ion selective membrane 38 is an ion exchange membrane, a substantial amount of active agent 40 may bond to ion exchange groups 50 in the pores, cavities or interstices 48 of the outermost ion selective membrane 38.

An outer active agent membrane 54 is generally positioned such that it is in contact with the biological interface when the iontophoresis device 10 is in use. The outer active agent membrane 54 takes the form of a microporous membrane in which the pores 56 (only one called out in FIGS. 5, 6A, and 6B for the sake of clarity of illustration) are filled with a polyelectrolyte gel. In some embodiments, the polyelectrolyte gel takes the form of a cross-linked polyelectrolyte gel.

Dispersing a biologically active agent in a gel matrix may enhance the stability and availability of the agent and the amount of the agent that can be loaded into the membrane. In some embodiments, hydrogels are preferred because they inherently contain significant amount of water, which can serve as a hydrating reservoir and maintain the active agent in a hydrated state during iontophoresis. Particularly preferred are cross-linked polyelectrolyte gels, which may be used to fill or coat the pores of microporous membranes and provide an ion-selective medium to which charged active agents may bind.

The release and loading characteristics of an active agent 42 in a cross-linked polyelectrolyte gel matrix can be a function of a number of factors, including: the degree of the cross-linking of the gel, the pH environment, and the density of the negatively charged groups.

Advantageously, when an electrical field is applied, the iontophoretic device 8 causes protons to migrate from an electrolyte reservoir to the vicinity of the gel matrix loaded with, for example, positively charged active agents, thereby result in the dissociation of the active agents 42. The effect of the electrically induced pH shift, in combination with the electromotive force and/or current, promotes the migration and the release of the active agent 42. This mechanism will be described in more details in connection with the description of the iontophoresis device below.

In one embodiment, the polyelectrolyte gel matrix loaded with the active agent 42 can be incorporated in its gel form to fill the pores of the microporous membrane to yield a gel-filled membrane. In another embodiment, the polyelectrolyte gel matrix loaded with the active agent 42 can be applied to the surface of the pores of the microporous membrane to yield a gel-coated membrane.

In certain embodiments, the cross-linked microporous gel may alternatively only coat the surfaces of the pores 56 of the membrane. In certain embodiments, the polyelectrolyte gel has a net negative charge and is particularly suited for loading doses of a cationic active agent 42 in the active electrode assembly 12.

Protons are produced as an electrochemical product of the oxidation of water in the active electrode assembly 12. The electrical current-induced proton migration to the outer active agent membrane lowers the pH environment of the gel matrix and neutralizes the negative charges. The active agents 42 therefore become dissociated from the gel matrix and can be rapidly released under the electromotive force. Under the influence of the electromotive force or current, the anionic groups on the polyelectrolyte gel substantially pass ions of the same polarity as active agent 36, 40, 42, while substantially blocking ions of the opposite polarity. Thus, the outer active agent membrane 54 is charge selective. Where the active agent 36, 40, 42 is a cation (e.g., lidocaine), the outer active agent membrane 54 may take the form of a cation-exchange membrane, thus allowing the passage of the cationic active agent while blocking the back flux of the anions present in the biological interface, such as skin or mucous membrane.

The outer active agent membrane 54 may be an integral part of the iontophoretic device 10. Alternatively, the outer active agent membrane 54 may be applied to the outer surface 22 of the active electrode assembly prior to use of the iontophoresis device 10. In certain embodiments, the iontophoresis device 10 may be designed with a cavity to accommodate the outer active agent membrane 54.

The active agent 42 that fails to bond to the ion exchange groups of material 50 may adhere to the outer surface 44 of the outermost ion selective membrane 38 as the further active agent 42. Alternatively, or additionally, the further active agent 42 may be positively deposited on and/or adhered to at least a portion of the outer surface 44 of the outermost ion selective membrane 38, for example, by spraying, flooding, coating, electrostatically, vapor deposition, and/or otherwise. In some embodiments, the further active agent 42 may sufficiently cover the outer surface 44 and/or be of sufficient thickness to form a distinct layer 52. In other embodiments, the further active agent 42 may not be sufficient in volume, thickness, or coverage as to constitute a layer in a conventional sense of such term.

In some embodiments, the iontophoresis device 8 may further include an interfacial layer 55 adjacent to the outer active agent membrane 54. The interface layer 55 is configured to contact to the biological interface 18. The interface layer 55 may enhanced the delivery of active agents 40 to the biological interface 18.

The interface layer 55 may take the form of, for example, a porous membrane material. In some embodiments, the interface layer 55 takes the form of a gel, an adhesive, and the like. In some embodiments, the interface layer 55 may comprise monovalent ions of counter charge to that of the active agent membrane 54. In some embodiments, the interface layer 55 may include monovalent ions having the same valence and charge of the active agent 40 to be delivered.

The interface layer 55 may have a thickness of less than 100 µm. Factors to consider in designing the thickness of the interface layer 55 may include counter-ion capacity and the overall physical strength of the resulting membrane. Further related properties of the interfacial layer 55 are described below.

The active agent 42 may be deposited in a variety of highly concentrated forms such as, for example, solid form, nearly saturated solution form, or gel form. If in solid form, a source of hydration may be provided, either integrated into the active electrode assembly 12, or applied from the exterior thereof just prior to use.

In some embodiments, the active agent 36 stored in optional inner active agent reservoir, additional active agent 40 stored in optional outer ion selective membrane 38, and/or active agent 42 may be identical or similar compositions or elements. In other embodiments, the active agent 36, additional active agent 40, and/or active agent 42 may be different compositions or elements from one another. Thus, a first type of active agent may be stored in the inner active agent reservoir 34, while a second type of active agent may be cached in the outer ion selective membrane 38. In such an embodiment, either the first type or the second type of active agent may be deposited in the outer active agent membrane 54 as active agent 42. Alternatively, a mix of the first and the second types of active agent may be deposited in the outer active agent membrane 54 as active agent 42. As a further alternative, a third type of active agent composition or element may be deposited in the outer active agent membrane 54 as active agent 42. In another embodiment, a first type of active agent may be stored in the inner active agent reservoir 34 as the active agent 36 and cached in the outer ion selective membrane 38 as the additional active agent 40, while a second type of active agent may be deposited in the outer active agent membrane 54 as active agent 42. Typically, in embodiments where one or more different active agents are employed, the active agents 36, 40, 42 will all be of common polarity to prevent the active agents 36, 40, 42 from competing with one another. Other combinations are possible.

The outer release liner 46 may generally be positioned overlying or covering the outer active agent membrane 54. The outer release liner 46 may protect the outer active agent membrane 54 during storage, prior to application of an electromotive force or current. The outer release liner 46 may be a selectively releasable liner made of waterproof material, such as release liners commonly associated with pressure sensitive adhesives. Note that the inner release liner 46 is shown in place in FIG. 5 and removed in FIG. 6.

In the embodiment illustrated in FIGS. 5, 6A, and 6B, the counter electrode assembly 14 comprises, from an interior 64 to an exterior 66 of the counter electrode assembly 14: a counter electrode element 68, an electrolyte reservoir 70 storing an electrolyte 72, an inner ion selective membrane 74, an optional buffer reservoir 76 storing buffer material 78, an optional outermost ion selective membrane 80, and an optional outer release liner (not shown).

The counter electrode element 68 is electrically coupled to a second pole 16b of the power source 16, the second pole 16b having an opposite polarity to the first pole 16a. In one embodiment, the counter electrode element 68 is an inert electrode. For example, the counter electrode element 68 may take the form of the carbon-based electrode element discussed above.

The electrolyte reservoir 70 may take a variety of forms including any structure capable of retaining electrolyte 72, and in some embodiments may even be the electrolyte 72 itself, for example, where the electrolyte 72 is in a gel, semi-solid or solid form. For example, the electrolyte reservoir 70 may take the form of a pouch or other receptacle, or a membrane with pores, cavities, or interstices, particularly where the electrolyte 72 is a liquid.

The electrolyte 72 is generally positioned between the counter electrode element 68 and the outermost ion selective membrane 80, proximate the counter electrode element 68. As described above, the electrolyte 72 may provide ions or donate charges to prevent or inhibit the formation of gas bubbles (e.g., hydrogen or oxygen, depending on the polarity of the electrode) on the counter electrode element 68 and may prevent or inhibit the formation of acids or bases or neutralize the same, which may enhance efficiency and/or reduce the potential for irritation of the biological interface 18.

The inner ion selective membrane 74 is positioned between and/or to separate, the electrolyte 72 from the buffer material 78. The inner ion selective membrane 74 may take the form of a charge selective membrane, such as the illustrated ion exchange membrane that substantially allows passage of ions of a first polarity or charge while substantially blocking passage of ions or charge of a second, opposite polarity. The inner ion selective membrane 74 will typically pass ions of opposite polarity or charge to those passed by the outermost ion selective membrane 80 while substantially blocking ions of like polarity or charge. Alternatively, the inner ion selective membrane 74 may take the form of a semi-permeable or microporous membrane that is selective based on size.

The inner ion selective membrane 74 may prevent transfer of undesirable elements or compounds into the buffer material 78. For example, the inner ion selective membrane 74 may prevent or inhibit the transfer of hydroxy ($OH^-$) or chloride ($Cl^-$) ions from the electrolyte 72 into the buffer material 78.

The optional buffer reservoir 76 is generally disposed between the electrolyte reservoir and the outermost ion selective membrane 80. The buffer reservoir 76 may take a variety of forms capable of temporarily retaining the buffer material

78. For example, the buffer reservoir 76 may take the form of a cavity, a porous membrane, or a gel. The buffer material 78 may supply ions for transfer through the outermost ion selective membrane 42 to the biological interface 18. Consequently, the buffer material 78 may comprise, for example, a salt (e.g., NaCl).

The outermost ion selective membrane 80 of the counter electrode assembly 14 may take a variety of forms. For example, the outermost ion selective membrane 80 may take the form of a charge selective ion exchange membrane. Typically, the outermost ion selective membrane 80 of the counter electrode assembly 14 is selective to ions with a charge or polarity opposite to that of the outermost ion selective membrane 38 of the active electrode assembly 12. The outermost ion selective membrane 80 is therefore an anion exchange membrane, which substantially passes anions and blocks cations, thereby prevents the back flux of the cations from the biological interface. Examples of suitable ion exchange membranes include the previously discussed membranes.

Alternatively, the outermost ion selective membrane 80 may take the form of a semi-permeable membrane that substantially passes and/or blocks ions based on size or molecular weight of the ion.

The outer release liner (not shown) may generally be positioned overlying or covering an outer surface 84 of the outermost ion selective membrane 80. The outer release liner may protect the outermost ion selective membrane 80 during storage, prior to application of an electromotive force or current. The outer release liner may be a selectively releasable liner made of waterproof material, such as release liners commonly associated with pressure sensitive adhesives. In some embodiments, the outer release liner may be coextensive with the outer release liner (not shown) of the active electrode assembly 12.

The iontophoresis device 8 may further comprise an inert molding material 86 adjacent exposed sides of the various other structures forming the active and counter electrode assemblies 12, 14. The molding material 86 may advantageously provide environmental protection to the various structures of the active and counter electrode assemblies 12,14. Enveloping the active and counter electrode assemblies 12, 14 is a housing material 90.

As best seen in FIG. 6B, the active and counter electrode assemblies 12, 14 are positioned on the biological interface 18. Positioning on the biological interface may close the circuit, allowing electromotive force to be applied and/or current to flow from one pole 16a of the power source 16 to the other pole 16b, via the active electrode assembly, biological interface 18 and counter electrode assembly 14.

In the presence of the electromotive force and/or current, a small amount of electrochemically-produced protons migrate from the electrolyte reservoir 26 across the inner ion (anion) selective membrane 30 to the inner active agent reservoir 34. The presence of the protons neutralizes the negatively charged gel matrix 33, causing the cationic active agent 36 to dissociate from the gel matrix, and be transported toward the biological interface 18. Optionally, additional active agent 40 is released by the ion exchange groups or material 50 by the substitution of ions of the same charge or polarity (e.g., active agent 36), and transported toward the biological interface 18. While some of the active agent 36 may substitute for the additional active agent 40, some of the active agent 36 may be transferred through the outer ion elective membrane 38 into the biological interface 18. Further optional active agent 42 carried by the outer surface 44 of the outer ion elective membrane 38 is also transferred to the biological interface 18.

In use, the outermost active electrode ion selective membrane 38 may be placed directly in contact with the biological interface 18. Alternatively, an interface-coupling medium (not shown) may be employed between the outermost active electrode ion selective membrane 22 and the biological interface 18. The interface-coupling medium may take, for example, the form of an adhesive and/or gel. The gel may take, for example, the form of a hydrating gel or a hydrogel. If used, the interface-coupling medium should be permeable by the active agent 36, 40, 42.

In some embodiments, the power source 16 is selected to provide sufficient voltage, current, and/or duration to ensure delivery of the one or more active agents 36, 40, 42 from the reservoir 34 and across a biological interface (e.g., a membrane) to impart the desired physiological effect. The power source 16 may take the form of one or more chemical battery cells, super- or ultra-capacitors, fuel cells, secondary cells, thin film secondary cells, button cells, lithium ion cells, zinc air cells, nickel metal hydride cells, and the like. The power source 16 may, for example, provide a voltage of 12.8 V DC, with tolerance of 0.8 V DC, and a current of 0.3 mA. The power source 16 may be selectively, electrically coupled to the active and counter electrode assemblies 12,14 via a control circuit, for example, via carbon fiber ribbons. The iontophoresis device 8 may include discrete and/or integrated circuit elements to control the voltage, current, and/or power delivered to the electrode assemblies 12, 14. For example, the iontophoresis device 8 may include a diode to provide a constant current to the electrode elements 24, 68.

As suggested above, the one or more active agents 36, 40, 42 may take the form of one or more ionic, cationic, ionizeable, and/or neutral drugs or other therapeutic agents. Consequently, the poles or terminals of the power source 16 and the selectivity of the outermost ion selective membranes 38, 80 and inner ion selective membranes 30, 74 are selected accordingly.

During iontophoresis, the electromotive force across the electrode assemblies, as described, leads to a migration of charged active agent molecules, as well as ions and other charged components, through the biological interface into the biological tissue. This migration may lead to an accumulation of active agents, ions, and/or other charged components within the biological tissue beyond the interface. During iontophoresis, in addition to the migration of charged molecules in response to repulsive forces, there is also an electroosmotic flow of solvent (e.g., water) through the electrodes and the biological interface into the tissue. In certain embodiments, the electroosmotic solvent flow enhances migration of both charged and uncharged molecules. Enhanced migration via electroosmotic solvent flow may occur particularly with increasing size of the molecule.

In certain embodiments, the active agent may be a higher molecular weight molecule. In certain aspects, the molecule may be a polar polyelectrolyte. In certain other aspects, the molecule may be lipophilic. In certain embodiments, such molecules may be charged, may have a low net charge, or may be uncharged under the conditions within the active electrode. In certain aspects, such active agents may migrate poorly under the iontophoretic repulsive forces, in contrast to the migration of small more highly charged active agents under the influence of these forces. These higher molecular weight active agents may thus be carried through the biological interface into the underlying tissues primarily via electroosmotic solvent flow. In certain embodiments, the high molecular weight polyelectrolytic active agents may be proteins, polypeptides, or nucleic acids. In other embodiments, the active agent may be mixed with another agent to form a complex capable of being transported across the biological interface via one of the motive methods described above.

In some embodiments, the transdermal drug delivery system 6 includes an iontophoretic drug delivery device 8 for providing transdermal delivery of one or more therapeutic active agents 36, 40, 42 to a biological interface 18. The delivery device 8 includes active electrode assembly 12 including at least one active agent reservoir and at least one active electrode element operable to provide an electromotive force to drive an active agent from the at least one active agent reservoir. The delivery device 8 may include a counter electrode assembly 14 including at least one counter electrode element 68, and a power source 16 electrically coupled to the at least one active and the at least one counter electrode elements 20, 68. In some embodiments, the iontophoretic drug delivery 8 may further include one or more active agents 36, 40, 42 loaded in the at least one active agent reservoir 34.

Figure 6C:
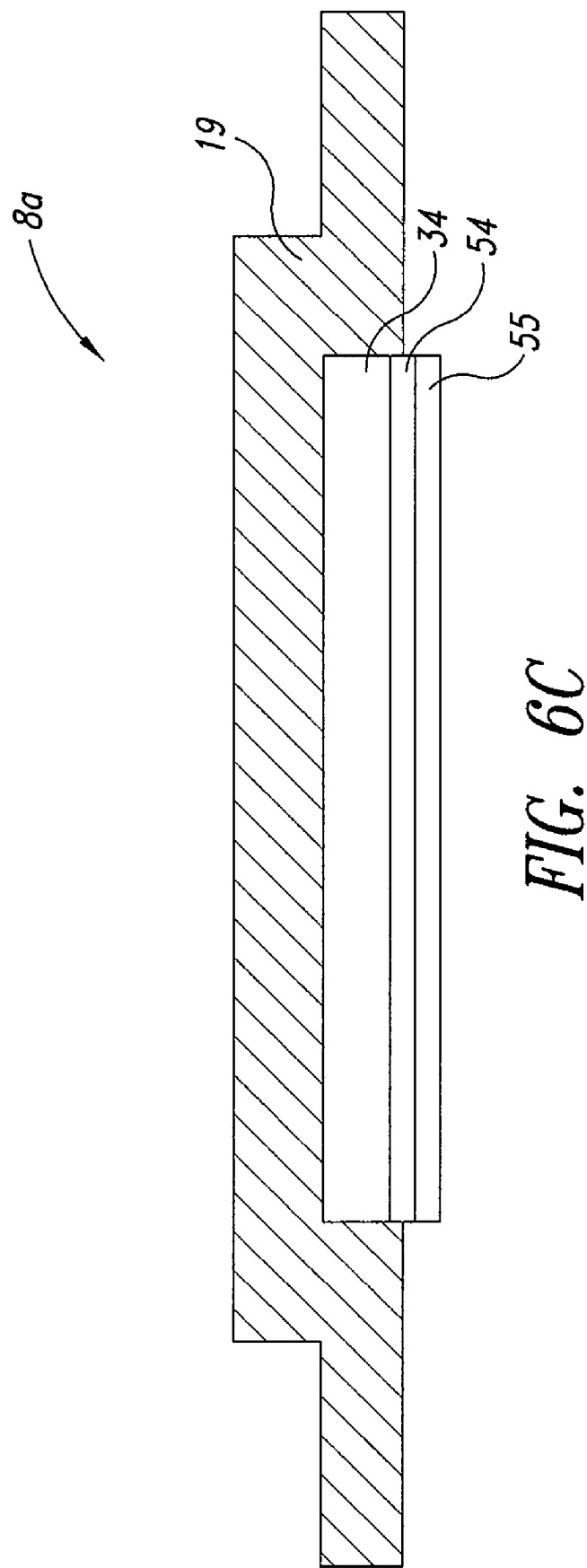
FIG. 6C is a schematic diagram of transdermal delivery device of according to another illustrated embodiment.

FIG. 6C shows an exemplary transdermal delivery device 8a for delivering active agents to a biological interface 18. The transdermal delivery device 8a includes an active agent reservoir 34, an outer active agent membrane 54, and an interfacial layer 55. The transdermal delivery device 8a may further include a backing layer 19.

In some embodiments, the transdermal delivery device 8a is configured to provide passive delivery of an active agent 40 stored in the active agent reservoir 34, and included in the outer active agent membrane 54.

The interfacial layer 55 may enhance the passive diffusion of an ionic active agent stored in, for example, an ion-exchange membrane.

The interfacial layer 55 is configured to form an interface layer next to the biological interface 18, when the transdermal delivery device 8a is placed on the biological interface 18 of a subject.

The interface layer 55 may take the form of, for example, a porous membrane material. In some embodiments, the interface layer 55 takes the form of a gel, an adhesive, and the like. In some embodiments, the interface layer 55 may comprise monovalent ions of counter charge of the active agent membrane 54. In some embodiments, the interface layer 55 may include monovalent ions having the same valence and charge of the active agent 40 to be delivered.

The interface layer 55 may have a thickness of less than about 100 μm. Factors to consider in designing the thickness of the interface layer 55 include: counter-ion capacity; and the overall physical strength of the resulting membrane. In some embodiments, the interface layer 55 may include monovalent ions of counter charge of the active agent membrane 54 (same valence and charge of the drug species to be delivered) and a thickness of less than approximately 100 μm. In some embodiments, the thickness of the interface layer 55 is substantially less than 100 μm. In some embodiments, the interface layer 55 may take the form of a spray-on adhesive, a tacky gel, and the like.

In some embodiments, the outer active agent membrane 54 takes the form of an ion-exchange membrane of a first polarity, and the interfacial layer 55 comprises a plurality of monovalent ions of a second polarity opposite to the first polarity of the ion-exchange membrane. In some embodiments, the first and the second active agents are the same.

The outer active agent membrane 54 may take the form of an ion-exchange membrane. In some embodiments, the outer active agent membrane 54 is monovalent with an exchange capacity from 0.8-1.6 mmol/g. The outer active agent membrane 54 may have a thickness of about approximately 100 μm and may be configured to maintain flexibility, yet have sufficient ionic drug capacity.

The active agent reservoir 34, may comprise a variety of materials including those previously mentioned, as well as, for example, adsorbent cotton, polyester felt, gel-like materials, and the like. In some embodiments, the active agent reservoir 34 may have capacity of about 5% to about 50% of the total molar equivalent, and at saturation concentration of the medium employed.

The transdermal delivery device 8a may function along general diffusion principals. The concentration of the active agent 40 within the outer active agent membrane 54, however, is typically much higher than can be achieved in aqueous solution. Accordingly, as the active agent 40 exits at the interfacial layer 55, the concentration is at saturation level and is maintained at that level until the outer active agent membrane 54 is depleted. The co-ions of the same valence within the interfacial layer 55 may diffuse into the outer active agent membrane 54 (e.g., ion-exchange membrane) and displace the active agent 40 from the outer active agent membrane 54. Applicants have found that having the interfacial layer 55 may play an important role for proper function.

The co-ions should have a significantly higher affinity for the outer active agent membrane 54 as opposed to the bound drug. With limitation to theory, it is believed that as the co-ions diffuse in the opposite direction (skin interface layer through the membrane and into the reservoir layer) they displace the drug ion from the outer active agent membrane 54. The drug ions subsequently enter the interfacial layer 55. The concentration of the drug in the interfacial layer 55 is determined by the diffusion coefficients through the various layers 34, 54. (In general, complex multi-laminate structures with widely varying partition coefficients are typically lumped together and reported under a single entity called a permeability coefficient.) The diffusion of the drug is limited by its physico-chemical properties, but in general the diffusion is governed by Fickian diffusion where the rate is driven by the concentration gradient. Without the co-ion impregnated interfacial layer 55, minimal amount of drug is released as a counter-potential is formed by the Donnan effect. This generally occurs when charge separation induced by the selectivity of the ion-exchange membrane forms a potential gradient across the membrane inhibiting further diffusion of the drug out of the outer active agent membrane 54. When this occurs, limited drug is released into the interface 55 adjacent to the outer active agent membrane 54 (e.g., an ion-exchange membrane). However, with the inclusion of smaller co-ions with greater affinity for the outer active agent membrane 54 into the interfacial layer 55, the co-ions displace the bound drug ions and may allow them to diffuse into the interfacial layer 55 at high concentration which in turn causes increased diffusion (delivery.) In some embodiments, this effect may likely be enhanced by the used of co-ion salts with lipophilic counter-ions which can act as penetration enhancers. This effect may be two-fold. The lipid counter-ions can insert themselves into the lipid lamellae that exist between the corneocytes of the stratum corneum and cause a temporary (reversible) disruption of the lamellae. This may allow swelling of the lamellae by body water and increases diffusion of hydrophilic species. This may also increase the diffusion of salts such as NaCl present in the body's water to diffuse into the interfacial layer and continue to assist in release of drug from the outer active agent membrane 54.

As mentioned above, lipophilic salts formed with a co-ion of high membrane affinity (small monovalent species) may likely give increased enhancement by working to disrupt the lipid layers in the skin and increasing is hydrophilic character or perhaps allowing ion-pair transport across the skin.

In selecting a suitable interface layer 55, the following factors may be considered: its penetration enhancing activity (via lipid layer disruption or ion-pair transport); and its ability to increase its partition coefficient in the interfacial layer (increases its solubility vs. aqueous solution.)

In selecting a suitable outer active agent membrane 54 the following factors should be considered: the capacity of the ion-exchange membrane (typically high capacity will likely work best as they have the ability to bind drug in greater "concentration"); and the thickness of the membrane. In some cases, the thickness of the membrane may not be important as the reservoir can continue to supply drug.

Figure 7:
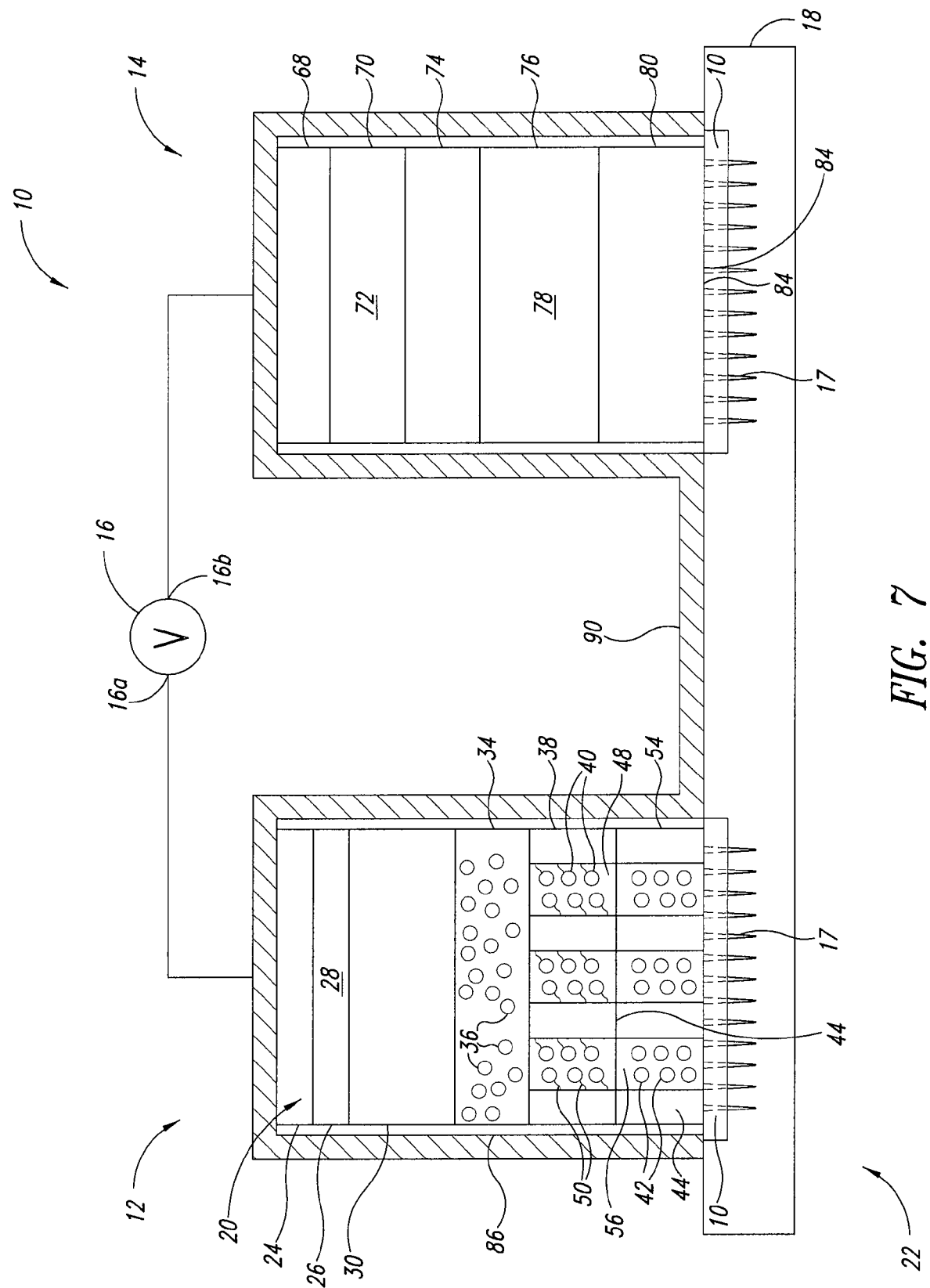
FIG. 7 is a schematic diagram of the iontophoresis device comprising an active and counter electrode assemblies and a plurality of microneedles according to one illustrated embodiment.

As shown in FIG. 7, the delivery device 8 may further include a substrate 10 including a plurality of microneedles 17 in fluidic communication with the active electrode assembly 12, and positioned between the active electrode assembly 12 and the biological interface 18. The substrate 10 may be positioned between the active electrode assembly 12 and the biological interface 18. In some embodiments, the at least one active electrode element 20 is operable to provide an electromotive force to drive an active agent 36, 40, 42 from the at least one active agent reservoir 34, through the plurality of microneedles 17, and to the biological interface 18.

Figure 8A:
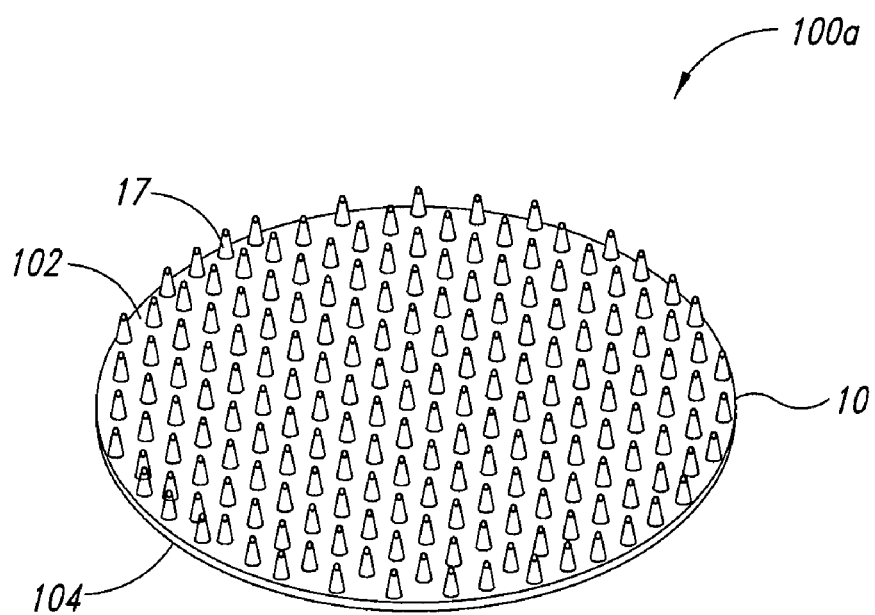
FIG. 8A is a bottom, front view of a plurality of microneedles in the form of an array according to one illustrated embodiment.
Figure 8B:
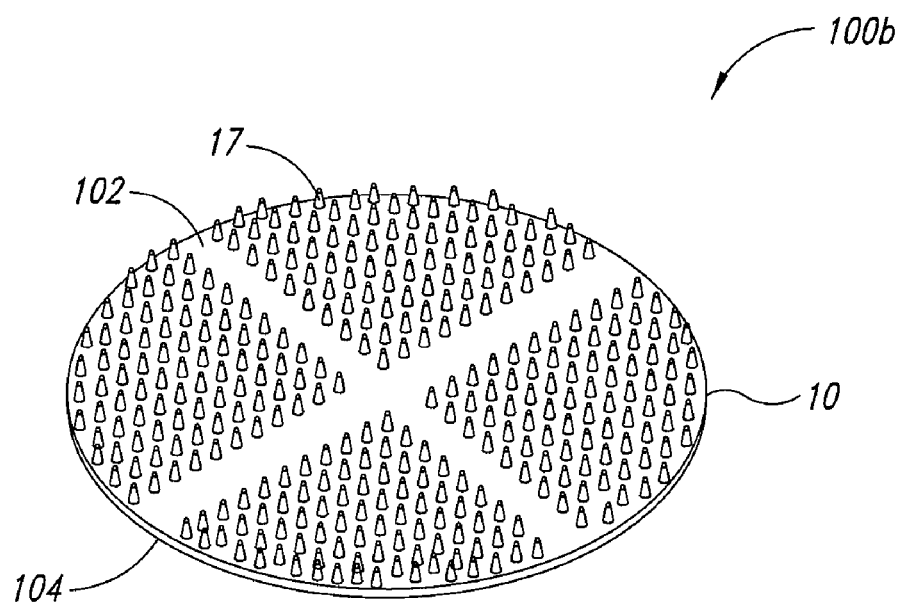
FIG. 8B is a bottom, front view of a plurality of microneedles in the form of one or more arrays according to another illustrated embodiment.

As shown in FIGS. 8A and 8B, the substrate 10 includes a first side 102 and a second side 104 opposing the first side 102. The first side 102 of the substrate 10 includes a plurality of microneedles 17 projecting outwardly from the first side 102. The microneedles 17 may be individually provided or formed as part of one or more arrays. In some embodiments, the microneedles 17 are integrally formed from the substrate 10. The microneedles 17 may take a solid and permeable form, a solid and semi-permeable form, and/or a solid and non-permeable form. In some other embodiments, solid, non-permeable, microneedles may further comprise grooves along their outer surfaces for aiding the transdermal delivery of one or more active agents. In some other embodiments, the microneedles 17 may take the form of hollow microneedles. In some embodiments, the hollow microneedles may be filled with ion exchange material, ion selective materials, permeable materials, semi-permeable materials, solid materials, and the like.

The microneedles 17 are used, for example, to deliver a variety of pharmaceutical compositions, molecules, compounds, active agents, and the like to a living body via a biological interface, such as skin or mucous membrane. In certain embodiments, pharmaceutical compositions, molecules, compounds, active agents, and the like may be delivered into or through the biological interface. For example, in delivering pharmaceutical compositions, molecules, compounds, active agents, and the like via the skin, the length of the microneedle 17, either individually or in arrays 100a, 100b, and/or the depth of insertion may be used to control whether administration of a pharmaceutical compositions, molecules, compounds, active agents, and the like is only into the epidermis, through the epidermis to the dermis, or subcutaneous. In certain embodiments, the microneedle 17 may be useful for delivering high-molecular weight active agents, such as those comprising proteins, peptides and/or nucleic acids, and corresponding compositions thereof. In certain embodiments, for example, wherein the fluid is an ionic solution, the microneedles 17 can provide electrical continuity between the power source 16 and the tips of the microneedles 17. In some embodiments, the microneedles 17, either individually or in arrays 100a, 100b, may be used to dispense, deliver, and/or sample fluids through hollow apertures, through the solid permeable or semi permeable materials, or via external grooves. The microneedles 17 may further be used to dispense, deliver, and/or sample pharmaceutical compositions, molecules, compounds, active agents, and the like by iontophoretic methods, as disclosed herein.

Accordingly, in certain embodiments, for example, a plurality of microneedles 17 in an array 100a, 100b may advantageously be formed on an outermost biological interface-contacting surface of a transdermal drug delivery system 6. In some embodiments, the pharmaceutical compositions, molecules, compounds, active agents, and the like delivered or sampled by such a system 6 may comprise, for example, high-molecular weight active agents, such as proteins, peptides, and/or nucleic acids.

In some embodiments, a plurality of microneedles 17 may take the form of a microneedle array 100a, 100b. The microneedle array 100a, 100b may be arranged in a variety of configurations and patterns including, for example, a rectangle, a square, a circle (as shown in FIG. 8A), a triangle, a polygon, a regular or irregular shapes, and the like. The microneedles 17 and the microneedle arrays 100a, 100b may be manufactured from a variety of materials, including ceramics, elastomers, epoxy photoresist, glass, glass polymers, glass/polymer materials, metals (e.g., chromium, cobalt, gold, molybdenum, nickel, stainless steel, titanium, tungsten steel, and the like), molded plastics, polymers, biodegradable polymers, non-biodegradable polymers, organic polymers, inorganic polymers, silicon, silicon dioxide, polysilicon, silicon rubbers, silicon-based organic polymers, superconducting materials (e.g., superconductor wafers, and the like), and the like, as well as combinations, composites, and/or alloys thereof. Techniques for fabricating the microneedles 17 are well known in the art and include, for example, electro-deposition, electro-deposition onto laser-drilled polymer molds, laser cutting and electro-polishing, laser micromachining, surface micro-machining, soft lithography, x-ray lithography, LIGA techniques (e.g., X-ray lithography, electroplating, and molding), injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, and the like), complementary-symmetry/metal-oxide semiconductor (CMOS) technology, deep x-ray exposure techniques, and the like. See for example, U.S. Pat. Nos. 6,256,533; 6,312,612; 6,334,856; 6,379,324; 6,451,240; 6,471,903; 6,503,231; 6,511,463; 6,533,949; 6,565,532; 6,603,987; 6,611,707; 6,663,820; 6,767,341; 6,790,372; 6,815,360; 6,881,203; 6,908,453; and 6,939,311. Some or all of the teachings therein may be applied to microneedle devices, their manufacture, and their use in iontophoretic applications. In some techniques, the physical characteristics of the microneedles 17 depend on, for example, the anodization conditions (e.g., current density, etching time, HF concentration, temperature, bias settings, and the like) as well as substrate properties (e.g., doping density, doping orientation, and the like).

The microneedles 17 may be sized and shaped to penetrate the outer layers of skin to increase its permeability and transdermal transport of pharmaceutical compositions, molecules, compounds, active agents, and the like. In some embodiments, the microneedles 17 are sized and shaped with an appropriate geometry and sufficient strength to insert into a biological interface (e.g., the skin or mucous membrane on a subject, and the like), and thereby increase a trans-interface (e.g., transdermal) transport of pharmaceutical compositions, molecules, compounds, active agents, and the like.

In certain embodiments, compounds or compositions can be delivered by an iontophoresis device comprising an active electrode assembly and a counter electrode assembly, electrically coupled to a voltage source to deliver an active agent to, into, or through a biological interface. The active electrode assembly includes the following: a first electrode member connected to a positive electrode of the voltage source; a active agent reservoir having a drug solution that is in contact with the first electrode member and to which is applied a voltage via the first electrode member; a biological interface contact member, which may be a microneedle array and is placed against the forward surface of the active agent reservoir; and a first cover or container that accommodates these members. The counter electrode assembly includes the following: a second electrode member connected to a negative electrode of the voltage source; a second electrolyte holding part that holds an electrolyte that is in contact with the second electrode member and to which voltage is applied via the second electrode member; and a second cover or container that accommodates these members.

In certain other embodiments, compounds or compositions can be delivered by an iontophoresis device comprising an active electrode assembly and a counter electrode assembly, electrically coupled to a voltage source to deliver an active agent to, into, or through a biological interface. The active electrode assembly includes the following: a first electrode member connected to a positive electrode of the voltage source; a first electrolyte holding part having an electrolyte that is in contact with the first electrode member and to which is applied a voltage via the first electrode member; a first anion-exchange membrane that is placed on the forward surface of the first electrolyte holding part; a active agent reservoir that is placed against the forward surface of the first anion-exchange membrane; a biological interface contacting member, which may be a microneedle array and is placed against the forward surface of the active agent reservoir; and a first cover or container that accommodates these members. The counter electrode assembly includes the following: a second electrode member connected to a negative electrode of the voltage source; a second electrolyte holding part having an electrolyte that is in contact with the second electrode member and to which is applied a voltage via the second electrode member; a cation-exchange membrane that is placed on the forward surface of the second electrolyte holding part; a third electrolyte holding part that is placed against the forward surface of the cation-exchange membrane and holds an electrolyte to which a voltage is applied from the second electrode member via the second electrolyte holding part and the cation-exchange membrane; a second anion-exchange membrane placed against the forward surface of the third electrolyte holding part; and a second cover or container that accommodates these members.

Aspects of the various embodiments can be modified, if necessary, to employ systems, circuits and concepts of the various patents, applications and publications to provide yet further embodiments, including those patents and applications identified herein. While some embodiments may include all of the membranes, reservoirs and other structures discussed above, other embodiments may omit some of the membranes, reservoirs or other structures. Still other embodiments may employ additional ones of the membranes, reservoirs and structures generally described above. Even further embodiments may omit some of the membranes, reservoirs and structures described above while employing additional ones of the membranes, reservoirs and structures generally described above.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including but not limited to: Japanese patent application Serial No. H03-86002, filed Mar. 27, 1991, having Japanese Publication No. H04-297277, issued on Mar. 3, 2000 as Japanese Patent No. 3040517; Japanese patent application Serial No. 11-033076, filed Feb. 10, 1999, having Japanese Publication No. 2000-229128; Japanese patent application Serial No. 11-033765, filed Feb. 12, 1999, having Japanese Publication No. 2000-229129; Japanese patent application Serial No. 11-041415, filed Feb. 19, 1999, having Japanese Publication No. 2000-237326; Japanese patent application Serial No. 11-041416, filed Feb. 19, 1999, having Japanese Publication No. 2000-237327; Japanese patent application Serial No. 11-042752, filed Feb. 22, 1999, having Japanese Publication No. 2000-237328; Japanese patent application Serial No. 11-042753, filed Feb. 22, 1999, having Japanese Publication No. 2000-237329; Japanese patent application Serial No. 11-099008, filed Apr. 6, 1999, having Japanese Publication No. 2000-288098; Japanese patent application Serial No. 11-099009, filed Apr. 6, 1999, having Japanese Publication No. 2000-288097; PCT patent application WO 2002JP4696, filed May 15, 2002, having PCT Publication No WO03037425; U.S. patent application Serial No. 2005/0070840, filed Aug. 24, 2004; Japanese patent application 2004/317317, filed Oct. 29, 2004; U.S. provisional patent application Ser. No. 60/627,952, filed Nov. 16, 2004; Japanese patent application Serial No. 2004-347814, filed Nov. 30, 2004; Japanese patent application Serial No. 2004-357313, filed Dec. 9, 2004; Japanese patent application Serial No. 2005-027748, filed Feb. 3, 2005; and Japanese patent application Serial No. 2005-081220, filed Mar. 22, 2005.

Aspects of the various embodiments can be modified, if necessary, to employ systems, circuits, and concepts of the various patents, applications, and publications to provide yet further embodiments.

These and other changes can be made in light of the above-detailed description. In general, in the following claims, the terms used should not be construed to be limiting to the specific embodiments disclosed in the specification and the claims, but should be construed to include all systems, devices and/or methods that operate in accordance with the claims. Accordingly, the invention is not limited by the disclosure, but instead its scope is to be determined entirely by the following claims.

What is claimed is:

1. A transdermal delivery device to passively deliver active agents to a biological interface, comprising:
   an active agent reservoir comprising a first active agent of a first polarity;
   an outer active agent membrane comprising a second active agent of the first polarity distributed therein, the outer active agent membrane taking the form of an ion-exchange membrane of a second polarity; and
   an interfacial layer having a first side adjacent to the outer active agent membrane and a second side configured to contact a biological interface, the interfacial layer comprising a plurality of freely diffusible monovalent co-ions of the first polarity.

2. The transdermal delivery device of claim 1 wherein the interfacial layer comprises a porous membrane material.

3. The transdermal delivery device of claim 2 wherein the interfacial layer takes the form of a gel or an adhesive.

4. The transdermal delivery device of claim 1 wherein the first polarity of the monovalent co-ions of the interfacial layer being opposite to the second polarity of the ion-exchange membrane.

5. The transdermal delivery device of claim 1 wherein the interfacial layer has a thickness of less than about 100 µm.

6. The transdermal delivery device of claim 1 wherein the first and the second active agents are the same.

7. The transdermal delivery device of claim 1 wherein the plurality of monovalent co-ions have lipophilic counter-ions.

8. The transdermal delivery device of claim 1 wherein the monovalent co-ions have a higher affinity than the second active agent has for the outer active agent membrane.

9. The transdermal delivery device of claim 1 wherein the monovalent co-ions are capable of diffusing to the outer active agent membrane and displacing the second active agent distributed therein.

* * * * *